US010488178B2

(12) United States Patent
Bouchard

(10) Patent No.: US 10,488,178 B2
(45) Date of Patent: Nov. 26, 2019

(54) FREQUENCY DOWN CONVERSION OPTICAL COHERENCE TOMOGRAPHY SYSTEM AND METHOD

(71) Applicant: INSTITUT NATIONAL D'OPTIQUE, Québec (CA)

(72) Inventor: Jean-Pierre Bouchard, Québec (CA)

(73) Assignee: INSTITUT NATIONAL D'OPTIQUE, Quebec (CA)

( * ) Notice: Subject to any disclaimer, the term of this patent is extended or adjusted under 35 U.S.C. 154(b) by 0 days.

(21) Appl. No.: 16/039,822

(22) Filed: Jul. 19, 2018

(65) Prior Publication Data

US 2019/0025042 A1 Jan. 24, 2019

Related U.S. Application Data

(60) Provisional application No. 62/535,351, filed on Jul. 21, 2017.

(51) Int. Cl.
*G01B 11/02* (2006.01)
*G01B 9/02* (2006.01)
*A61B 3/10* (2006.01)
*G01N 21/47* (2006.01)

(52) U.S. Cl.
CPC .......... *G01B 9/02091* (2013.01); *A61B 3/102* (2013.01); *G01N 21/4795* (2013.01)

(58) Field of Classification Search
CPC ............ G01B 9/02091; G01B 9/02083; G01B 9/02004; A61B 3/102; G01N 21/4795
USPC .................................................. 356/479, 497
See application file for complete search history.

(56) References Cited

U.S. PATENT DOCUMENTS

| 9,857,160 | B1* | 1/2018 | Hoffer, Jr. .......... G01B 9/02077 |
| 2013/0322721 | A1* | 12/2013 | Hogan ................. A61B 5/0033 382/131 |
| 2014/0024947 | A1 | 1/2014 | Barbato |
| 2015/0351635 | A1* | 12/2015 | Cerussi ............... A61B 5/0075 600/477 |
| 2016/0252340 | A1 | 9/2016 | Hollenbeck et al. |

(Continued)

OTHER PUBLICATIONS

Tyler S. Ralston et al., "Real-time digital design for an optical coherence tomography acquisition and processing system", SPIE, Jul. 2004, vol. 5324, pp. 159-170.

(Continued)

*Primary Examiner* — Tarifur R Chowdhury
*Assistant Examiner* — Jonathon Cook
(74) *Attorney, Agent, or Firm* — Maschoff Brennan

(57) ABSTRACT

An optical coherence tomography (OCT) system for imaging a sample is provided. The OCT system includes an optical circuit and a digitization circuit. The optical circuit includes an interferometer and is configured to probe the sample and generate an analog OCT signal representative of the sample. The digitization circuit includes a frequency down converter and an analog-to-digital converter. The digitization circuit is configured to receive, down convert and digitize the analog OCT signal, thereby outputting a digitized down converted signal. A method for imaging a sample is also provided. The method includes steps of optically probing the sample to generate the analog OCT signal representative of the sample and processing the analog OCT signal to obtain the digitized down converted signal.

25 Claims, 17 Drawing Sheets

(56) References Cited

U.S. PATENT DOCUMENTS

2017/0122722 A1 5/2017 Raymond et al.

OTHER PUBLICATIONS

Extended European Search Report, dated Sep. 17, 2018, for European application No. 18184538.9, 10 pages.
Biedermann, B. R. et al., Real time en face Fourier-domain optical coherence tomography with direct hardware frequency demodulation, Optics Letters, vol. 33, No. 21, p. 2556-2558, Nov. 1, 2008.
Davis, A. M. et al., Heterodyne swept-source optical coherence tomography for complete complex conjugate ambiguity removal, Journal of Biomedical Optics, vol. 10(6), 064005, p. 064005-1-064005-6, Nov./Dec. 2005.
Wang, Z. et al., Cubic meter volume optical coherence tomography, Optica, vol. 3, No. 12, p. 1496-1503, Dec. 2016.
Zurauskas, M. et al., Frequency multiplexed long range swept source optical coherence tomography, Biomedical Optics Express, vol. 4, No. 6, p. 778-788, Jun. 1, 2013.

* cited by examiner

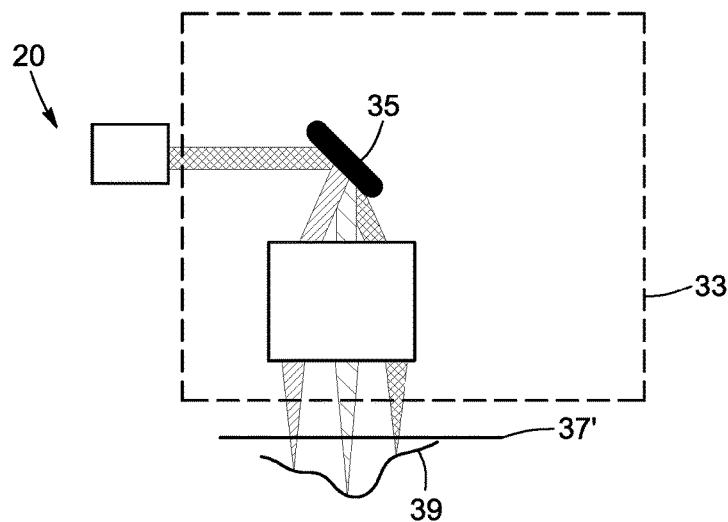
FIG. 6
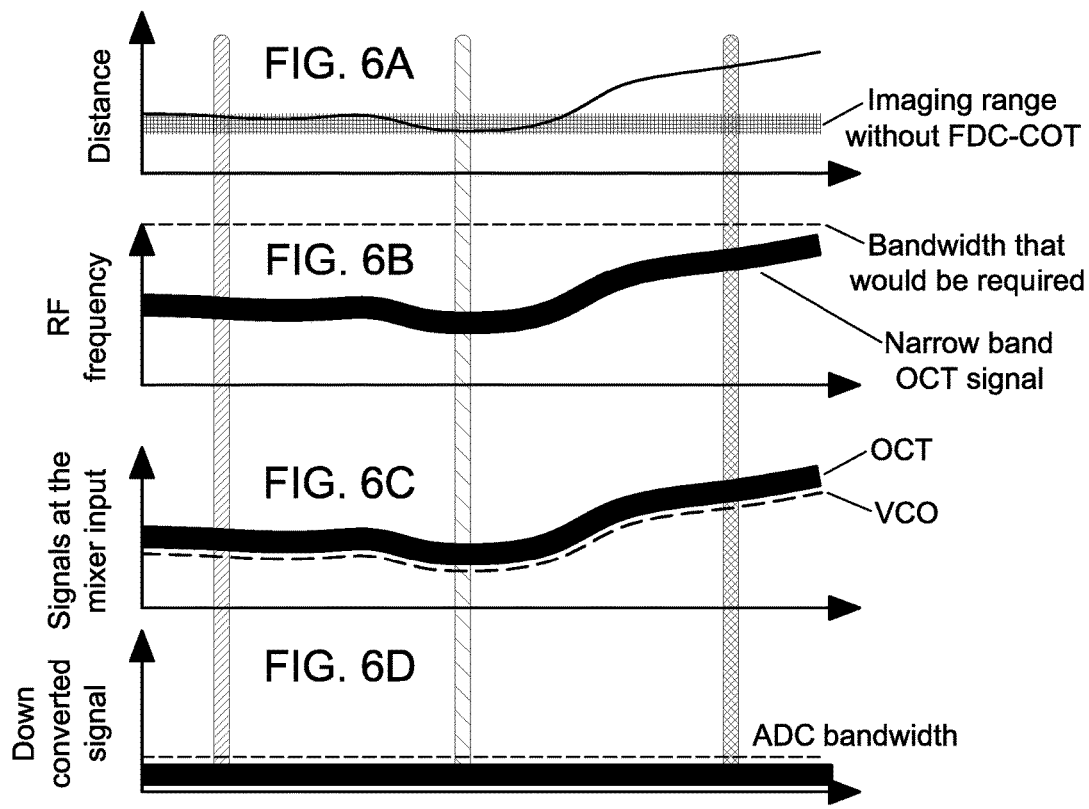

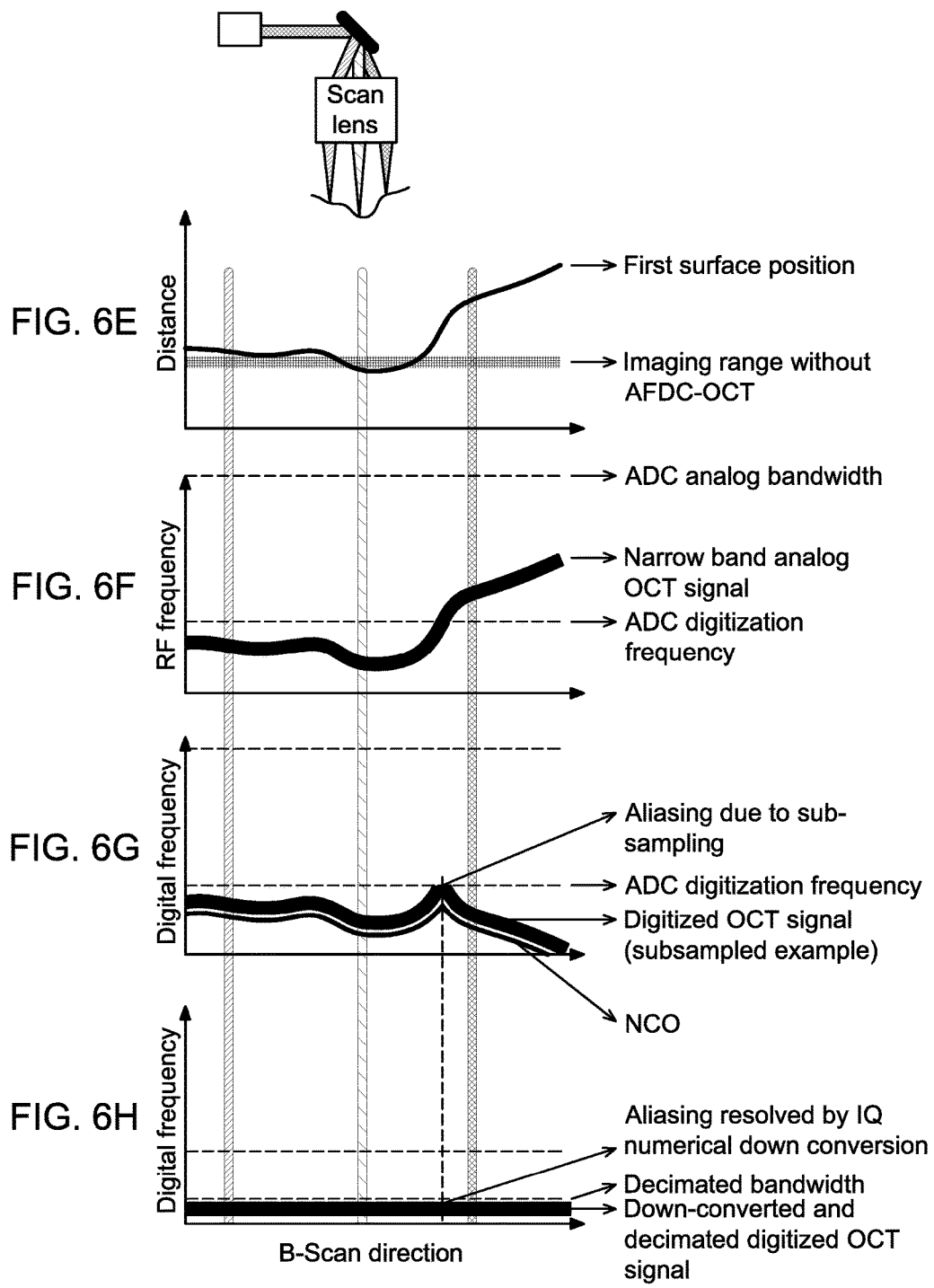

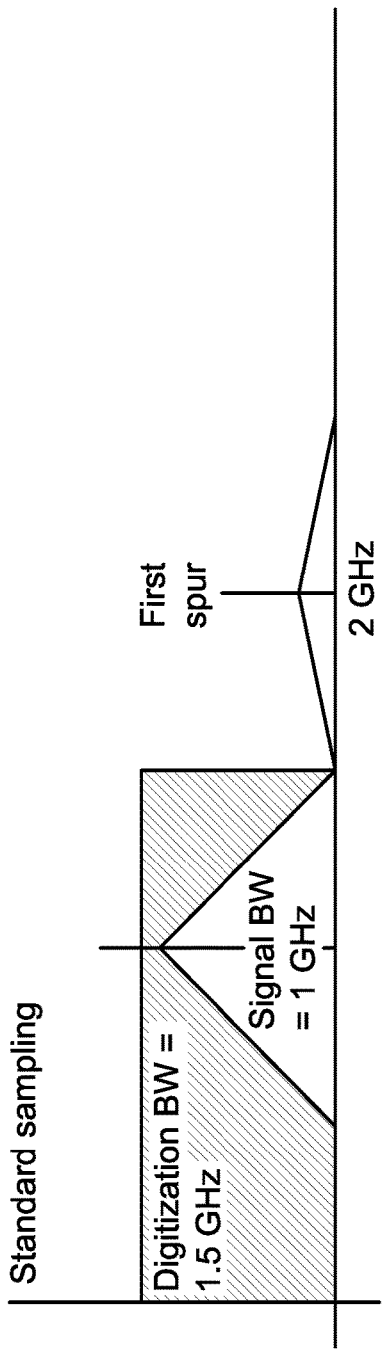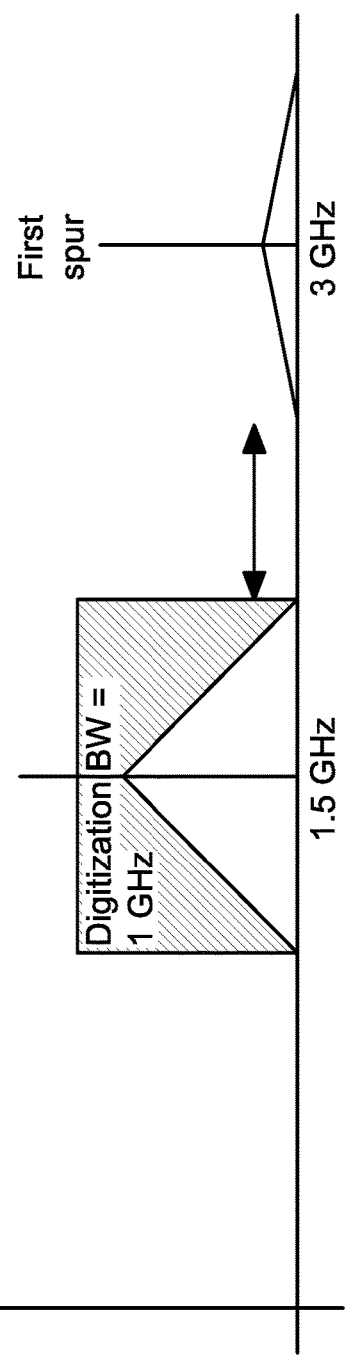

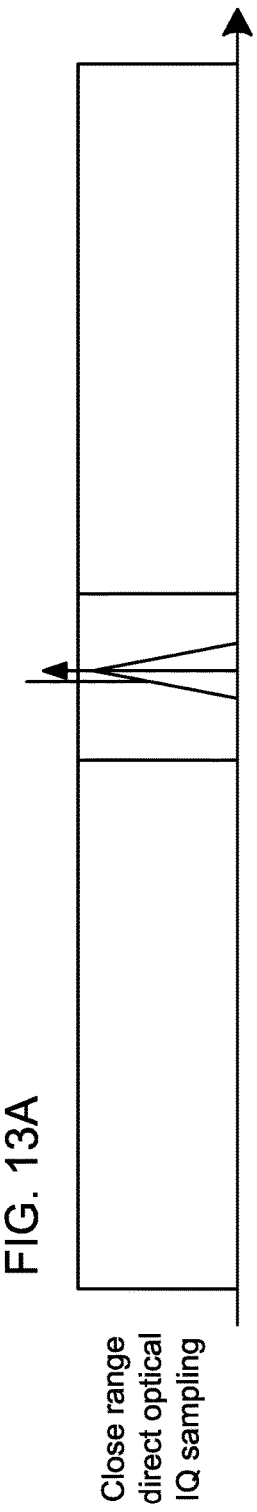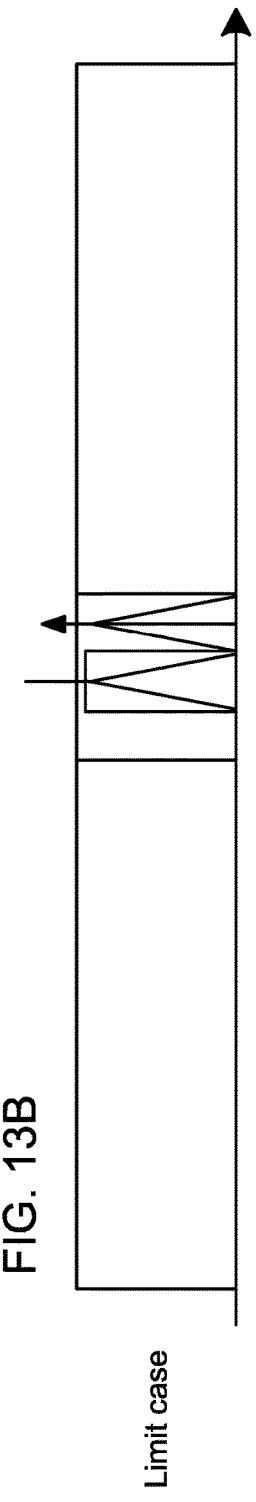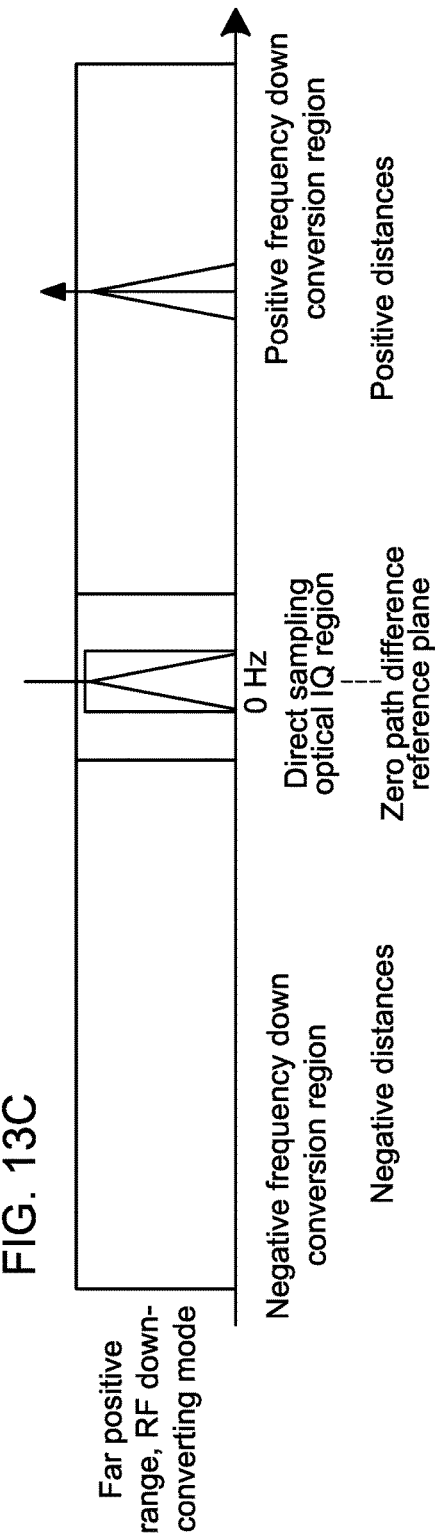

US 10,488,178 B2

FREQUENCY DOWN CONVERSION OPTICAL COHERENCE TOMOGRAPHY SYSTEM AND METHOD

TECHNICAL FIELD

The technical field generally relates to optical imaging applications, and more particularly concerns an optical coherence tomography system and related method with adjustable and adaptable working distance.

BACKGROUND

Optical coherence tomography (OCT) systems are known as being useful for producing high resolution and three-dimensional images of samples. Swept source optical coherence tomography (SS-OCT) systems are a subclass of OCT systems using a frequency-sweeping light source.

SS-OCT systems, such as the ones depicted in FIG. 1 (PRIOR ART), typically use a sweeping tunable laser to interrogate an optical interferometer. The sweeping tunable laser emits a laser beam towards the interferometer. The laser beam passes through a beam splitter and is separated into a sample beam and a reference beam. The sample beam (solid line) reaches and illuminates the sample (schematically illustrated as one individual scatterer on FIG. 1), and then returns back to the beam splitter before being reflected towards an optical detector. The reference beam (dashed line) propagates along the reference arm and is reflected by a plane reference mirror back towards the detector. The reference beam and the sample beam interfere on the photosensitive surface area of the detector, producing an electrical signal herein referred to as the "analog OCT signal". Due to the optical path length difference between the sample beam and the reference beam, and due to the sweeping of the optical emission frequency, the optical frequencies of the two beams reaching the detector differ by an amount $2 \times m/c$, where x is the optical path length difference, m the rate of change of the optical frequency and c the speed of light. The interference of these two beams on the detector will result in the OCT electrical signal at the difference of the two optical frequencies (associated to the reference beam and the sample beam—also called the "beat frequency" in the case of an individual scatterer).

A typical sample is however formed of multiple individual scatterers, and each individual scatterer illuminated by the sample beam contributes to the OCT electrical signal. Indeed, each individual scatterer is associated with its own optical path length difference and its corresponding beat frequency, so that interferometric beam is the result of the coherent sum of all those frequencies. The OCT electrical signal is therefore an analog representation of the optical interferometric beam envelope which correlates to the sample reflectivity profile along the sample beam propagation direction through a Fourier transform operation after applying the proper sweep nonlinearity corrections.

In many applications, SS-OCT systems may image a few hundred of microns within the sample (i.e., below the surface of the sample). This limitation is not imposed by the imaging range of the SS-OCT systems, but rather by the light attenuation within the sample. Indeed, even though an OCT system may have an imaging range of several millimeters or centimeters, the signal reflected by the sample is only coming from a section along the optical axis (typically a fraction of a millimeter) within the larger imaging range. This situation is depicted in FIG. 2.

FIG. 2 illustrates an interferometer configuration that may be included in an SS-OCT system. The situation depicted in FIG. 2 is one where the imaging range of the system is substantially larger than the penetration depth of the light within the sample. FIG. 2 also displays at line B a diagram illustrating the reflectivity profile of the sample along the optical axis (i.e., along the sample beam propagation direction). The light attenuation profile of the sample beam along the optical axis is also illustrated at line C, wherein the intensity of the sample beam with respect to the distance travelled through the sample is clearly represented. Line D shows the corresponding OCT electrical signal's spectrum. One skilled in the art would understand that, in the scenario depicted in FIG. 2, the center frequency of the OCT electrical signal, which could be, in some scenarios, in the RF range, is relatively high, while its bandwidth is relatively narrow (compared to the value around which is centered the OCT electrical signal).

It remains a challenge to measure samples presenting surface variations that exceed the imaging range of the SS-OCT systems of prior art. There is thus a need for a system for imaging such samples.

SUMMARY

In accordance with an aspect, there is provided an optical coherence tomography (OCT) system for imaging a sample. The OCT system includes an optical circuit and a digitization circuit. The optical circuit includes an interferometer. The optical circuit is configured to probe the sample and generate an analog OCT signal representative of the sample. The digitization circuit includes a frequency down converter and an analog-to-digital converter. The digitization circuit is configured to receive, down convert and digitize the analog OCT signal, thereby outputting a digitized down converted signal.

In some embodiments, the OCT system is designed as a swept source OCT system.

In some embodiments the OCT system includes a scanning head for scanning the sample, wherein the interferometer includes a reference arm and a sample arm optically coupled with the scanning head.

In some embodiments the OCT system includes at least one detector optically coupled with the optical circuit and operatively connected with the digitization circuit.

In some embodiments, the optical circuit is configured to generate multiple analog OCT signals and the digitization circuit includes multiple channels, each channel being configured to receive one of the multiple analog OCT signals.

In some embodiments, the OCT system includes a surface profiler for providing topological information about a surface of the sample.

In some embodiments, the analog-to-digital converter has a digitization bandwidth, and the system further includes a servo-loop configured to maintain the down converted signal within the digitization bandwidth.

In some embodiments, the analog-to-digital converter is configured to digitize the analog OCT signal, thereby obtaining a digital OCT signal and the frequency down converter is located downstream of the analog-to-digital converter and is configured to down convert the digital OCT signal into the digitized down converted signal.

In some embodiments, the digitization circuit includes a local signal generator for generating a local oscillator signal centered around a local frequency and a mixer operatively connected to the local signal generator configured to receive the digital OCT signal and mix the digital OCT signal with the local oscillator signal to obtain the digitized down converted signal.

In some embodiments, the local signal generator is a numerically-controlled oscillator.

In some embodiments, the OCT system includes a servo-loop configured to maintain the local frequency close to a frequency of the digital OCT signal.

In some embodiments, the frequency down converter is configured to down convert the analog OCT signal to a lower analog frequency signal and the analog-to-digital converter is located downstream of the analog frequency down converter and is configured to digitize the lower analog frequency signal, thereby obtaining the digitized down converted signal.

In some embodiments, the digitization circuit includes a local signal generator for generating a local oscillator signal centered around a local frequency and at least one mixer having a range of operation, the mixer being operatively connected to the local signal generator and being configured to receive the analog OCT signal and mix the analog OCT signal with the local oscillator signal to obtain the down converted signal.

In some embodiments, the local signal generator is a voltage-controlled oscillator.

In some embodiments, the local signal generator includes a plurality of voltage-controlled oscillators, each having a different bandwidth covering a corresponding portion of the range of operation of said at least one mixer, the digitization circuit further including a switch to operatively connect at least one of the plurality of the voltage-controlled oscillators to said at least one mixer.

In some embodiments, the digitization circuit includes a high frequency counter operatively connected to the local signal generator.

In some embodiments, the digitization circuit is designed to be compatible with quadrature modulation techniques.

In some embodiments, the at least one mixer is a pair of mixers and the system further includes a coupler operatively connected to the pair of mixers, the coupler being configured to generate an in-phase version and an in-quadrature version of the local oscillator signal, the pair of mixers being configured to generate an in-phase down converted signal and an in-quadrature down converted signal.

In some embodiments, the analog OCT signal has a frequency in the RF domain.

In accordance with another aspect, there is provided a method for imaging a sample. The method includes steps of optically probing the sample to generate an analog OCT signal representative of the sample and processing the analog OCT signal to obtain a digitized down converted signal.

In some embodiments, the step of processing the analog OCT signal includes digitizing the analog OCT signal to obtain a digital OCT signal, down converting the digital OCT signal to obtain the digitized down converted signal and digitally filtering the digital OCT signal.

In some embodiments, the method includes a step of decimating the digitized down converted signal.

In some embodiments, the step of processing the analog OCT signal includes down converting the analog OCT signal to a lower analog frequency signal, filtering the lower analog frequency signal in the analog domain and digitizing the lower analog frequency signal to obtain the digitized down converted signal.

In some embodiments, the method includes a step of monitoring with a high frequency counter, during an A-scan, a local frequency of a local oscillator signal generated by a local oscillator general.

In accordance with another aspect, there is provided an optical tomography system for imaging a sample. The system includes a tunable light source, an optical module, a frequency down conversion module, and a digital module. The optical module probes the sample and generates an OCT electrical signal typically having a frequency in the RF domain representative of the sample. The frequency down conversion module receives and down converts the OCT electrical signal to a down converted signal. The center frequency of the down converted signal is lower frequency than that of the OCT electrical signal. The digital module digitizes the down converted signal.

In accordance with another aspect, there is provided an OCT system for imaging a sample having multiple individual scatterers. The OCT system includes an SS-OCT apparatus. The SS-OCT apparatus has an imaging range. The sample is translucent (or in some cases optically transparent) to at least a range of optical frequencies (or corresponding wavelengths), and has surface variations that exceed the imaging range of the SS-OCT apparatus.

The OCT system includes an acquisition and control card operatively connected to the SS-OCT apparatus. The acquisition and control card includes at least one analog-to-digital converter (ADC), each having a sampling rate. The SS-OCT apparatus probes the samples with a sample beam and generates an OCT electrical signal processed by the acquisition and control card at the sampling rate (i.e. by one of the at least one ADC). In this sense, the imaging range of the SS-OCT apparatus is limited by the sampling rate of the ADC. For OCT systems that have a substantially long imaging range, the OCT electrical signal is characterized by a substantially narrow spectral band (i.e. has a narrow spectral width), and is centered at a high center frequency (compared to the narrow spectral band) that may be too high to be digitized by the ADC. The narrow spectral width of the OCT electrical signal depends on a penetration depth of the sample beam in the sample (i.e. under its surface), while the OCT electrical signal high center frequency depends on an optical path difference associated with the sample surface distance with respect to the plane representing zero path difference.

The OCT system includes a frequency down conversion module for down converting the OCT electrical signal into a down converted signal. The frequency down conversion module is operatively connected with the SS-OCT apparatus and the acquisition and control card. The frequency down conversion module is configured to "translate" (i.e. down convert) the OCT electrical signal down to the down converted signal before its transmission to the acquisition and control card. The down converted signal is centered around a lower center frequency. The down converted signal is preferably obtained by mixing the OCT electrical signal with a local oscillator signal (LO signal), so as to generate the down converted signal, also known in mixer terminology as an "intermediate frequency" ("IF") signal. The intermediate frequency signal has a spectral profile comparable to the spectral profile of the OCT electrical signal, but is centered around the lower center frequency. The lower center frequency is less demanding for the sampling rate of the ADC. The ADC digitizes the down converted signal, instead of the OCT electrical signal directly outputted by the SS-OCT apparatus.

In accordance with one implementation, there is provided an optical coherence tomography system for imaging a sample having multiple individual scatterers with a tunable light source generating a laser beam. The system includes an optical module, a detection unit, a frequency down conversion module and a digital module.

The optical module is operatively connected with the light source. The optical module includes an interferometer for receiving the laser beam and for transmitting an optical interferometric beam representative of the sample. Each individual scatterer is associated to an optical path difference and a corresponding frequency, and contributes to the optical interferometric beam. The detection unit is coupled with the optical module and receives the optical interferometric beam. The detection unit generates an OCT electrical signal. The OCT electrical signal results from the sum of all the corresponding frequencies associated with the individual scatterer at the detection unit. In some applications (e.g. in long imaging range applications), the OCT electrical signal has a substantially narrow spectral band (i.e. has a narrow spectral width), and is centered at a high center frequency (compared to the narrow spectral band).

The frequency down conversion module is operatively connected to the detection unit. The frequency down conversion module includes a local signal generator and a mixer. The local signal generator is configured to generate a local oscillator signal. The local oscillator signal is centered around a local frequency. The mixer is operatively connected to the detection unit and to the local signal generator. The mixer is configured to mix the OCT electrical signal and the local oscillator signal, and to produce a down converted signal centered around a lower center frequency. The digital module is configured to digitize the down converted signal.

Broadly, embodiments of the system presented herein shows some advantages over the conventional SS-OCT system, and so may improve some features of the SS-OCT systems. In operation, the system may be used for establishing a depth mapping of samples (i.e. profiling samples) being translucent or optically transparent to at least some wavelength(s) or at least one waveband.

Other features and advantages of the present description will become more apparent upon reading of the following non-restrictive description of specific embodiments thereof, given by way of example only with reference to the accompanying drawings.

BRIEF DESCRIPTION OF THE DRAWINGS

FIGS. 6 and 6A-H are a schematized representation of a use of the frequency down converting OCT system of the FIG. 2 in the context of measuring a sample presenting surface variations larger than the imaging range. FIGS. 6A-D present an analog implementation. FIG. 6E-H present a digital implementation.

FIGS. 11A-B show the standard sampling and the bandpass sampling techniques achievable with the frequency down converting OCT system, in accordance with one embodiment

FIGS. 13A-C illustrate a frequency down conversion mode and a standard digitization mode, both achievable with the frequency down converting OCT system, in accordance with one embodiment.

DETAILED DESCRIPTION

Figure 1:
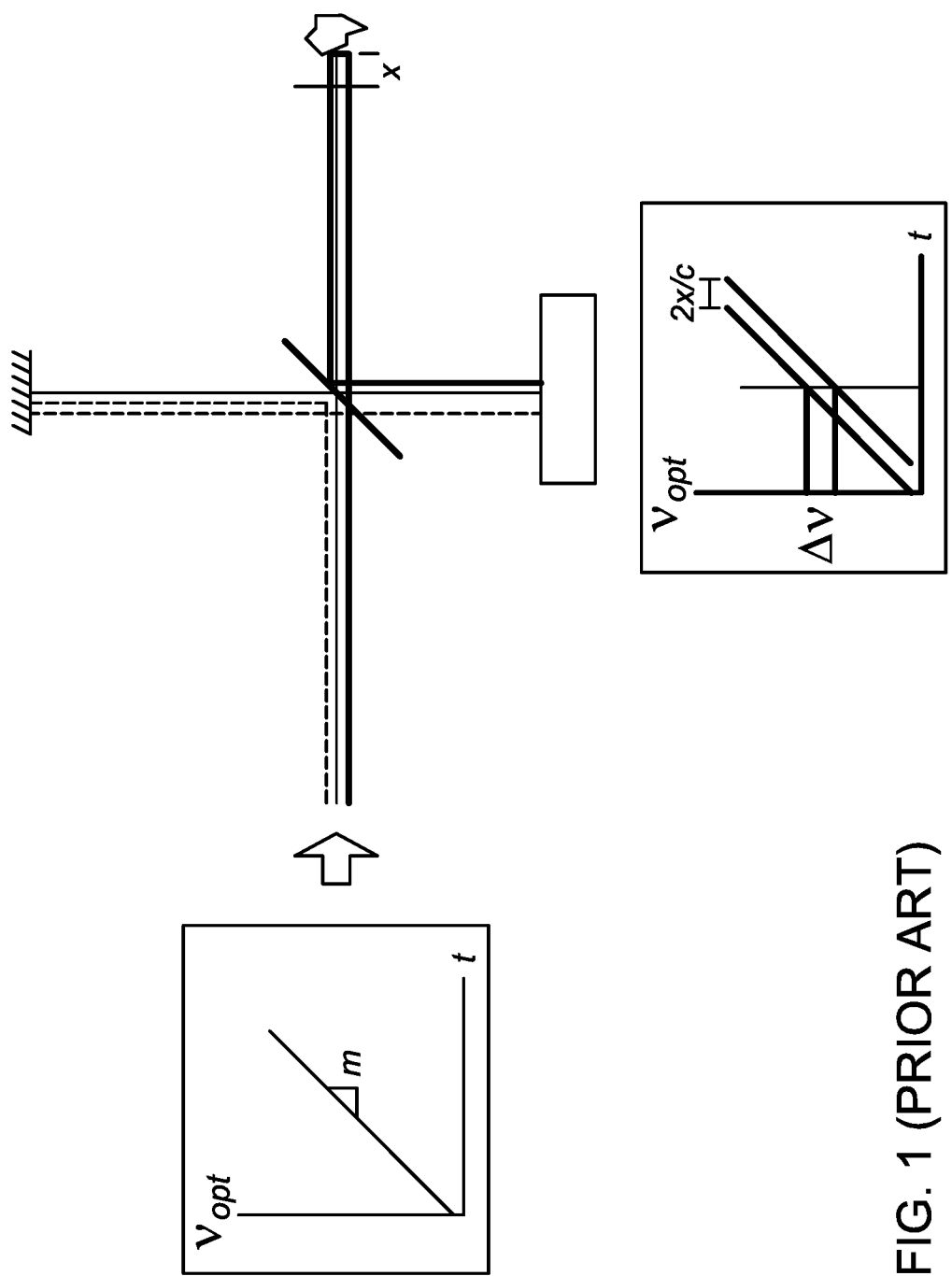
FIG. 1 illustrates the operating principle of an SS-OCT apparatus for imaging a sample (PRIOR ART).
Figure 2:
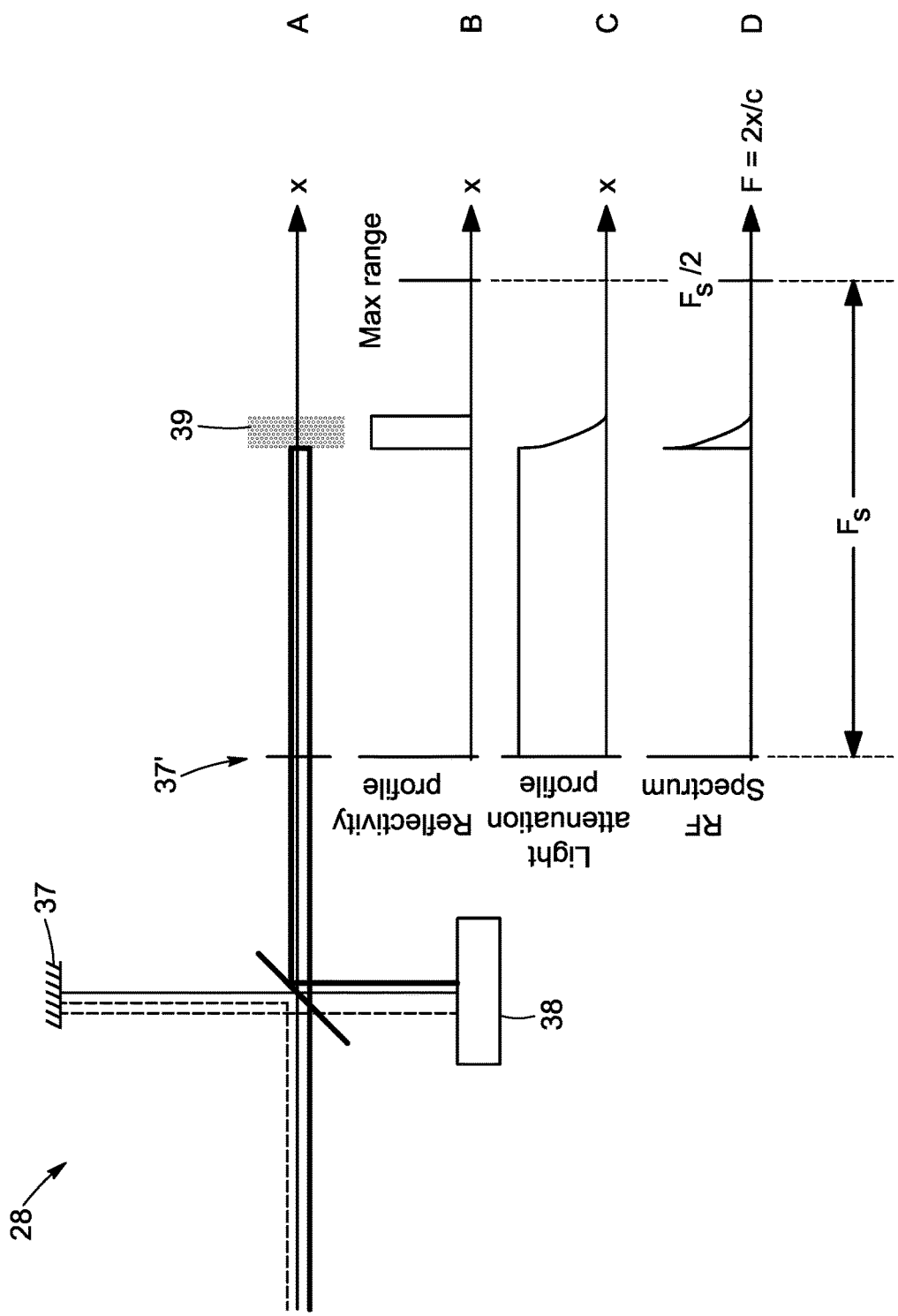
FIG. 2 (lines A-D) illustrates an SS-OCT apparatus for imaging a sample and graphical representations of the reflectivity profile, the light attenuation profile and the radio-frequency spectrum representative of the sample (PRIOR ART).

In the following description, similar features in the drawings have been given similar reference numerals, and, to not unduly encumber the figures, some elements may not be indicated on some figures if they were already identified in one or more preceding figures. It should also be understood herein that the elements of the drawings are not necessarily depicted to scale, since emphasis is placed upon clearly illustrating the elements and structures of the present embodiments.

The term "tunable" is herein understood to refer to the ability to adjust and select, i.e., "tune", "select" or "adjust" spectral and other features of a beam and/or signal, such as the operating wavelength, the band-pass, and the like. In this context, a tunable light source may emit a "tunable laser beam".

The terms "connected", "coupled", "operatively connected" and variants and derivatives thereof, refer to any connection or coupling, either direct or indirect, between two or more elements. The connection or coupling between the elements may be mechanical, physical, optical, operational, electrical or a combination thereof.

In the present description, the terms "light" and "optical", "spectral profile" and "waveband", derivatives and variants thereof, are used to refer to radiation in any appropriate region of the electromagnetic spectrum and, more particularly, are not limited to visible light. By way of example, in some embodiments, the terms may encompass electromagnetic radiation with a wavelength ranging from about 800 to 1600 nm. More particularly, although some implementations of the present techniques can be useful in near-infrared applications, other embodiments could additionally or alternatively operate in other regions of the electromagnetic spectrum, for example in the millimeter, terahertz, visible and ultraviolet regions.

The term "transparent" (and variants thereof, such as "optically transparent") refers in the following to a property of transmitting at least a portion, and in some case the entirety of one or more region(s) of the electromagnetic spectrum (i.e. the property of not absorbing a significant portion of one or more region(s) of the electromagnetic spectrum). In some scenario, the sample may be said to be transparent.

The term "translucent" refers to the property of transmitting and diffusing at least a portion, and in some case the entirety of one or more region(s) of the electromagnetic spectrum. In the context of a diffusing sample, the sample may be said to be translucent.

It is also noted, and unless otherwise mentioned, that terms such as "substantially", "centered around" and "about" that modify a value, condition or characteristic of a feature of an exemplary embodiment, should be understood to mean that the value, condition or characteristic is defined within tolerances that are acceptable for proper operation of this exemplary embodiment for its intended application.

The present description generally relates to an optical coherence tomography system and related method with adjustable and adaptable working distance. More particularly, the OCT system includes an optical circuit and a digitization circuit. The digitization circuit includes a frequency down converter and an analog-to-digital converter. The frequency down converter is configured to convert the OCT signal to a lower frequency more compatible with typical sample frequencies of digitization devices (e.g., analog-to-digital converter), which may be useful for imaging samples presenting surface variations, and/or uneven or curved surfaces, and/or to provide a broader range of position(s) at which the sample may be positioned with respect to the OCT system.

The description will also make use of the following expressions:

"Imaging range" refers to the imaging range supported by the sampling rate of the analog-to-digital converter (or similar device). In the context of an OCT system or SS-OCT apparatus, it corresponds to the available depth of a single A-scan. As such, the imaging range may also be referred to as "instantaneous imaging range" or "sampling rate-limited range".

"Working distance" herein typically refers to the distance between the part of the system that directs the sample beam towards the sample and the closest point of the imaging range. In the case of a conventional SS-OCT, the working distance corresponds to the distance between the part of the system that directs the sample beam towards the sample and the image of the reference mirror. In the case of the SS-OCT presented in the current description, the working distance may be varied through frequency down conversion. In some implementations, the SS-OCT system is configured to differentiate the positive frequencies from the negative frequencies. In these implementations, the reference mirror typically corresponds to the center of the imaging range, rather than the closest point of the imaging range.

"Working distance range" refers to the extent over which the imaging range may be displaced along the optical axis of the sample beam. As will be explained below, in some implementations a variation of the frequency of a local signal generator such as a voltage-controlled oscillator (VCO) allows to displace the imaging range applicable for different A-scans to providing imaging capability over a much longer imaging distance.

"Laser beam" is the beam of light emitted by the tunable light source. In this context, the laser beam is a tunable laser beam.

"Sample beam" is the portion of the laser beam which is directly or indirectly (e.g. after a passage through a beam splitter) sent towards the sample. The expression may also refer to the portion of the laser beam reflected by the sample.

"Reference beam" is the portion of the laser beam which is directly or indirectly (e.g. after a passage through a beam splitter) sent towards a reference mirror. The expression may also refer to the portion of the laser beam reflected by the reference mirror.

"Optical interferometric beam" is the beam resulting from the interference between the sample beam and the reference beam. The optical interferometric beam has a spectral profile representative of the sample. Each individual scatterer of the sample contributes to the optical interferometric beam "Time-varying envelope" refers to the slowly varying optical electric field amplitude envelope of the optical interferometric beam. It may also be referred to as the "optical interferometric beam envelope".

"OCT signal" is the signal at the output of a detector combined with or integrated to the SS-OCT system. In the present disclosure, the OCT signal can either be an "analog OCT signal" or a "digital OCT signal", the latter being obtained when the analog OCT signal is converted to a digital OCT signal, e.g., using an analog-to-digital converter. It is to be noted that, in the context of radio communications, the analog OCT signal is typically referred to as a "radio frequency (RF) signal". The analog OCT signal has a spectral profile that is an analog representation of the time-varying envelope of the optical interferometric beam and is therefore representative of the reflectivity profile of the sample along the propagation direction of the sample beam through a Fourier transform. In some contexts, the analog OCT signal may result from the coherent sum of all the corresponding frequency associated with the individual scatterer at the detector(s) (sometimes referred to as a "detection unit").

"Digitized down converted signal" refers to the digitized down converted version of the analog OCT signal. In the context of radio communications, the digitized down converted signal may be referred to as an "intermediate frequency" (IF) signal.

Frequency Down Conversion Optical Coherence Tomography System

The system presented in the following section relies on the frequency down conversion process to bring a high frequency and narrow band OCT signal down to a lower frequency. In some implementations, which will be generally referred to as "analog implementations", the frequency down conversion process may allow digitization of the lower frequency at a lower rate than what would be required to digitize the "original" signal (i.e., the OCT signal). In other implementations, which will be generally referred to as "digital implementations", the situation is somewhat different, as it will be introduced in one of the following sections.

The system is a "frequency down conversion swept source OCT system" and will be simply referred to as "the system" or as "the OCT system".

As already known by one skilled in the art, the expression "frequency conversion" refers to the signal processing technique creating new frequencies by mixing at least two frequencies. This technique may be useful for shifting a frequency, for example from a first frequency to a second lower frequency. In such case, the "frequency conversion" is said to be a "frequency down conversion" (and conversely, the conversion from a first frequency to a second higher frequency would be said to be a "frequency up conversion"). The frequency down conversion process is an exemplary application of what may also be known in the art as the "heterodyning process".

More particularly, and as it will be described with greater details below, the OCT system presented herein can be designed as an SS-OCT system, and is provided with a digitization circuit configured such that the imaging range of the OCT system may be "modulated" (i.e., displaced in frequency, and, for example and without being limitative, down converted), resulting in an extended working distance range for the system. Such an extended working distance range may be useful, for example, when investigating a sample presenting surface variations larger that the imaging range of the SS-OCT apparatus, because the working distance of the OCT system may be adjusted and adapted between each A-scan. In some scenarios, the OCT system may also be useful for characterizing substantially flat sample. In such scenarios, the working distance may vary from one B-scan to another. The modulation of the working distance may be then used as a "fast autofocus".

General Overview of the OCT System

Figure 3:
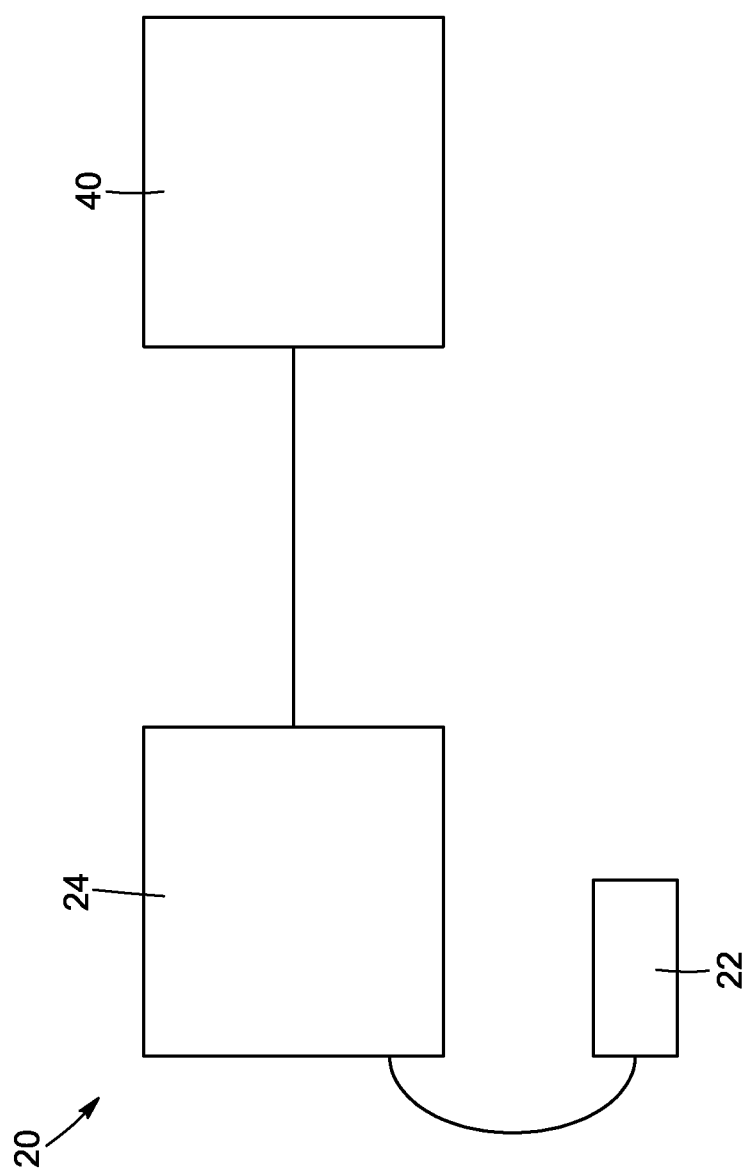
FIG. 3 is a schematized representation of a frequency down converting OCT system for imaging a sample according to one embodiment.

Turning to FIG. 3, a simplified schematic of an optical coherence tomography (OCT) system 20 for imaging a sample is shown. As illustrated, the OCT system 20 includes an optical circuit 24 and a digitization circuit 40. The OCT system is also provided with a light source 22.

Broadly described, the optical circuit 24 is configured to probe the sample and generate an analog OCT signal representative of the sample. The digitization circuit 40 is configured to receive, down convert and digitize the analog OCT signal, and subsequently outputting a down converted signal.

Figure 4:
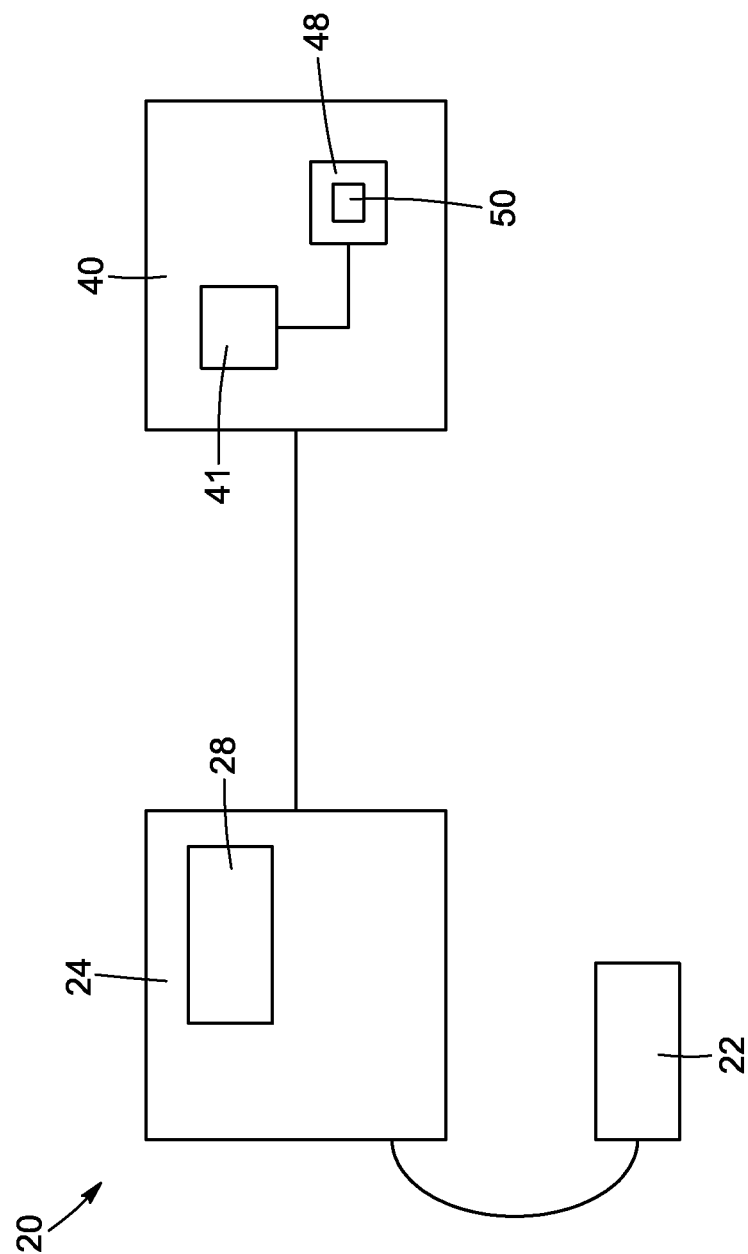
FIG. 4 is a schematized representation of a frequency down converting OCT system for imaging a sample according to one embodiment.

With reference to FIG. 4, the optical circuit 24 includes an interferometer 28. The digitization circuit includes a frequency down converter 41 and an analog-to-digital converter 50 (sometimes referred to as the "ADC 50").

In some embodiments, the ADC 50 is part of a digital module 48.

It is to be noted that, in some implementations, at least one of the light source 22, the optical circuit 24 and the digitization circuit 40 may be of conventional design. In some embodiments, the OCT system 20 is designed as a swept source OCT system.

By way of example and without being limitative to the scope of the invention, various embodiments of the OCT system 20 and its components will now be described.

Light Source

As illustrated in FIGS. 3 and 4, the system 20 includes a light source 22 generating a laser beam. The light source 22 is a tunable light source generating a tunable laser beam. In some embodiments, the tunable light source may be embodied by a tunable laser configured to substantially linearly sweep its output optical frequency over a portion of a tuning range. The laser beam coherence length has to be long enough, and, for example and without being limitative, is generally longer than a maximal optical path difference (e.g., between a reference path and a sample path). The light source 22 may also be substantially linearly swept without mode hopping and swept fast enough to support the A-Scan rate required for the targeted applications.

It will be readily understood that the requirements for the optical frequency (or corresponding wavelength) of the laser beam may depend on the targeted application(s), and so is not specific to (i.e., is not an intrinsic characteristic of) the OCT system 20 disclosed herein. In some embodiments, the optical frequency may be in the terahertz portion of the electromagnetic spectrum (substantially corresponding to an IR portion of the electromagnetic spectrum). The optical frequency is then selected according to the availability of light sources (e.g., 850 nm, 1060 nm, 1310 nm, 1550 nm, or any other available light sources) and/or the characteristics of a sample (not shown in FIGS. 3 and 4) under investigation (e.g., its absorption).

It is to be noted that the light source 22 can be embodied by many different light sources and/or combinations thereof, for example, and without being limitative, vertical-cavity surface-emitting laser (VCSEL) with varying cavity length, semiconductor-based laser coupled with corresponding built in frequency selection structures such as tunable distributed Bragg reflectors, fiber laser, or any other light source meeting the requirements of the targeted applications.

Optical Circuit

Figure 5:
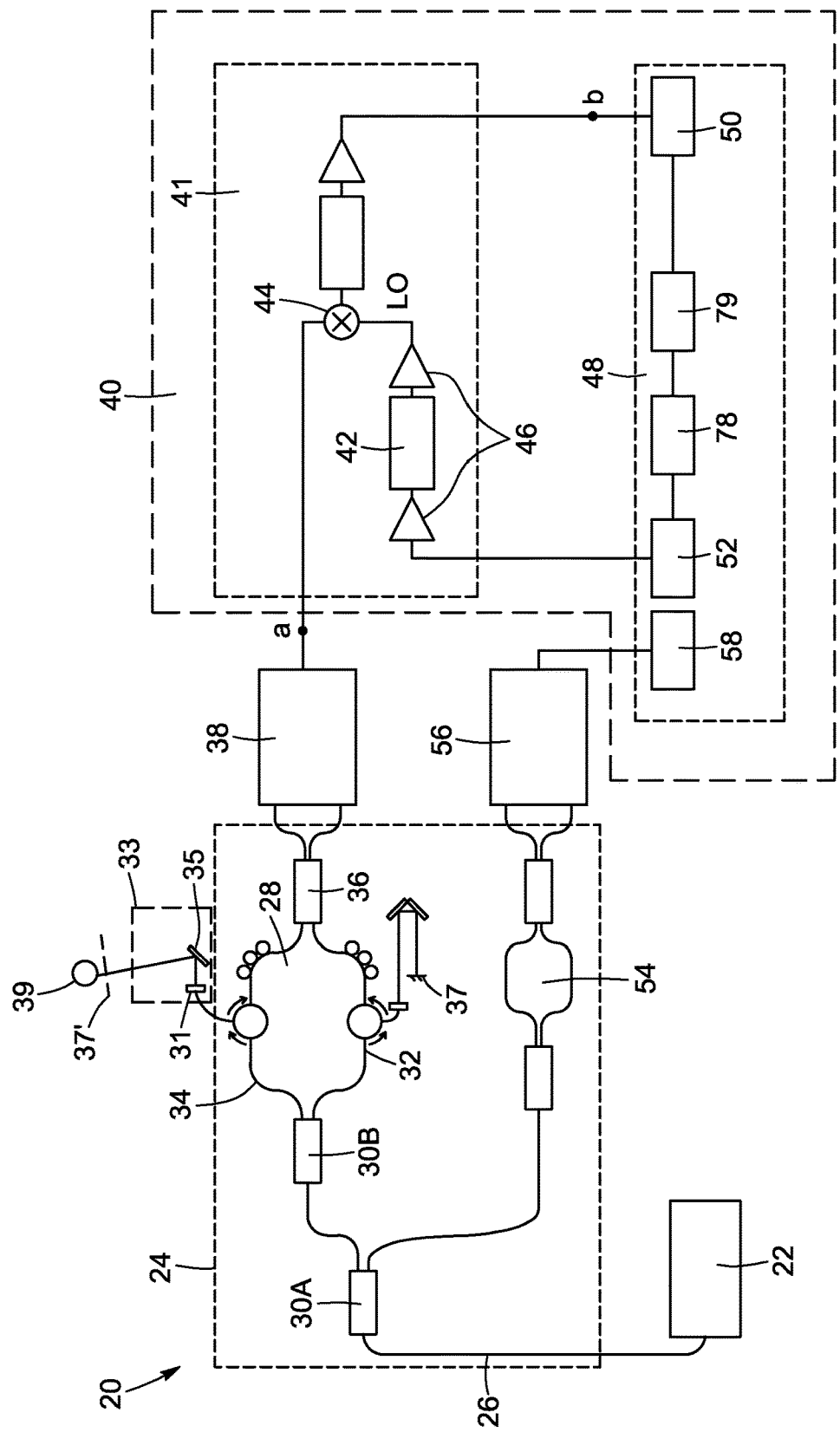
FIG. 5 is a schematized representation of a frequency down converting OCT system for imaging a sample according to one embodiment.

Now turning to FIG. 5, a non-limitative embodiment of the OCT system 20 is shown. The OCT system 20 includes an optical circuit 24 operatively connected to the light source 22, hence allowing the laser beam generated by the light source 22 to be sent towards the optical circuit 24 and its components.

For example, in some embodiments, an optical fiber 26 may be used to guide the laser beam from the light source 22 to the optical circuit 24. Other components and means for coupling the laser beam with the optical circuit 24 may be used, such as the ones already known by one skilled in the art. In some variants, the light source may be integrated into the optical circuit 24, so that the light source 22 and the optical circuit 24 may form a single device.

In the embodiment illustrated in FIG. 5, the optical circuit 24 includes an interferometer 28, which may be interrogated by the tunable light source 22. In this context, the light source 22 is rapidly sweeping its emission optical frequency, as it has previously been introduced.

In the illustrated configuration, the light source 22 is optically coupled with the interferometer 28. The coupling of the light source 22 with the interferometer 28 may be operated by any suitable optical components or combination of optical components, such as, but not limited to optical fiber(s), beam splitter(s), beam coupler(s), filter(s), combinations thereof, or any other components already known by one skilled in the art.

It is to be noted that the working principle of the optical circuit 24, and so its design, may be similar and in some scenario assimilated to the working principle and design of a conventional SS-OCT system.

Now that the coupling between the light source 22 and the optical circuit 24 has been described, the path of the laser beam within the optical circuit 24 will be presented.

In the illustrated embodiment, the optical circuit 24 includes a first beam splitter 30A to first separate the laser beam into two portions defining a measurement beam and a clocking beam.

The measurement beam is then incident on a second beam splitter 30B which again separates the measurement beam into two portions, defining a reference beam and a sample beam, which respectively follow a reference arm 32 and a sample arm 34 of the interferometer 28. The sample beam is incident on a sample 39, as it will be described in further detail below.

In operation, the sample 39 under investigation is placed in the sample arm 34. The sample beam reaches and irradiates the multiple individual scatterers of the sample 39. After its interaction with the sample 39, the sample beam is then reflected back towards the interferometer 28.

The reference beam follows the reference arm 32 and is reflected back towards the interferometer 28 by a reference mirror 37.

The interferometer 28 is configured to combine the resulting sample beam and reference beam into an optical interferometric beam representative of the reflectivity of the sample 39. The optical interferometric beam is outputted by the optical circuit 24. In the illustrated variant, the reference beam and the sample beam are coupled through a coupler 36. The coupler 36 is placed at the output of the interferometer 28, i.e., is positioned downstream of the interferometer 28.

It is to be noted that in the case of a single scatterer, the resulting sample beam and the reference beam interfere at a frequency, known in the art as a "beat frequency". This beat frequency is proportional to the distance x of the single scatterer from an image 37' of the reference mirror 37 along the sample beam path, to produce the optical interferometric beam. In the following, the image 37' of the reference mirror 37 will simply be referred to as the reference plane 37'.

However, in a more realistic case, the sample 39 has multiple individual scatterers, and each of the scatterers are disposed at a different distance depth within the sample 39. The reflected sample beam and the reflected reference beam interfere and produce a signal that is representative of a more complex reflectivity profile within the sample 39. Indeed, each individual scatterer contributes to the optical interferometric beam according to its own optical path difference and a corresponding beat frequency. As a result, in the scenario of the sample 39 having multiple scatterers, the optical interferometric beam has a complex envelope instead of a single beat frequency, due to the presence of the multiple individual scatterers within the sample 39. It is known in the prior art that Fourier analysis of this envelope may be performed to extract the reflectivity profile along the x direction into the sample 39.

As illustrated in the embodiment of FIG. 5, the OCT system 20 further includes a scanning head 33 coupled with the optical circuit 24 or a component thereof.

For example, the sample arm 34 of the interferometer 28 may be optically coupled with the scanning head 33 in order to displace the sample beam transversally to its optical axis in order to repeat the depth analysis at different regions of the sample 39.

In some embodiments, the scanning head 33 includes a scan mirror 35. The scan mirror 35 may be scanned in angle, thereby allowing to image a line across the sample 39 under investigation (referred to in the field as a "B-scan"). In alternate embodiments, other scanning configurations could be used.

In some implementations, the scanning head 33 may be moved independently from the OCT system 20 through a fiber connection. In other implementations, the scanning head 33 is integral to the system.

As illustrated, the scanning head 33 also includes a collimator 31 for collimating the sample beam onto the scan mirror 35, for example at the interface of an optical fiber and air, for instance in the scenario in which the interferometer 28 is fiber-based and component(s) of the scanning head 33 are free-space based.

Many other configurations of the interferometer 28 may be suitable for use in the optical circuit 24 of the system 20 described herein. For example, one skilled in the art may rely on a Michelson, a Linnik, a Mach-Zender, any other interferometer typically used in SS-OCT system, or a combination thereof, inasmuch as the interferometer 28 allows generating the optical interferometric beam that is representative of the sample 39 under investigation.

It is to be noted that the sample beam and the reference beam, as well as their corresponding reflected beams, and the optical interferometric beam, may be guided through optical components (e.g., optical fibers, filters, lenses, mirrors, other components, or combinations thereof). Indeed, in the illustrated embodiment, the interferometer 28 is a fiber-based interferometer. Alternatively, the interferometer 28 could also be a "free-space" interferometer (i.e., without fiber optics). The different possible configurations of the interferometer 28 and optical, electrical and/or mechanical components required to achieve such configurations are already known by one skilled in the art.

The optical circuit 24 may also include, for example, some other mechanical, optical and/or electronics components found in conventional SS-OCT systems. For example, the optical circuit 24, as illustrated in FIG. 5, generates only one optical interferometric beam (to be converted in a corresponding one OCT signal).

In other embodiments, the optical circuit 24 is configured to generate multiple analog OCT signals (i.e., more than one optical interferometric beam), to be digitized by the digitization unit, which comprises multiple channels, each channel being configured to receive one of the multiple analog OCT signals. This configuration can be used, for example and without being limitative, in the context of polarization sensitive OCT, where two polarizations of the light are detected separately. In another example, the optical circuit 24 may be configured to generate both an in-phase (I) and an in quadrature (Q) optical interferometric beam using optical configurations known in the art, which allows to lift the indetermination between the positive and negative frequencies, which in turn allows to double the possible imaging range for a given digitization bandwidth.

Detector

Still referring to FIG. 5, the OCT system 20 includes at least one detector. For example, the OCT system includes a first detector 38 coupled with the optical circuit 24.

The detector 38 is configured to convert the optical interferometric beam in a corresponding analog OCT signal representative of the reflectivity profile of the sample 39. In some embodiments, the analog OCT signal has a frequency in the RF domain.

The analog OCT signal typically has a spectral profile similar to the optical interferometric beam envelope. In the illustrated variant, the detector 38 is mounted near the optical circuit 24 and is more particularly coupled with the interferometer 28 through the coupler 36. The detector 38 is placed at the output and positioned downstream of the optical circuit 24.

In some embodiment, the detector 38 could comprise, for example, at least one photodetector. In some variants, the detector 38 is a balanced detector. However, while being useful to some variants, balanced detection is not necessary to the proper functioning of the OCT system 20.

In some implementations, the optical circuit 24 and detectors 38 are integrated into a single device or system, and are optically, electrically and/or mechanically connected through appropriate means and/or components. In these implementations, the device or system resulting from the combination of the optical circuit 24 and the detector 38 have the capabilities of the optical circuit 24 and the first detector 38.

Based on the remarks presented in a previous section, the greater is the distance between the reference mirror image 37' and the scatterers, the greater is the frequency around which is centered the analog OCT signal.

For example, in analog implementations, the imaging range attainable by conventional SS-OCT systems is typically limited by the rate at which the analog OCT signal can be digitized. In such circumstances, it may be useful to convert the analog OCT signal into a down converted signal having a lower center frequency. Although frequency down conversion allows for a lower digitization frequency, the frequency response of the detector 38 still has to be broad enough to cover the entire range of the analog OCT signal. The situation is somewhat different in the digital implementations, as it will be described in one of the following sections.

Now that the optical circuit 24 and the detector 38 have been presented, the digitization circuit 40 will be described in greater detail.

Digitization Circuit

As illustrated in FIGS. 3 and 4, the digitization circuit 40 includes a frequency down converter 41 and an ADC 50.

Analog-to-Digital Converter

Now referring to FIGS. 3 to 5, the OCT system 20 also includes, in some embodiments, a digital module 48.

The digital module 48 may include at least one analog-to-digital converter (ADC) and at least one digital-to-analog converter (DAC) or any other mean of controlling the frequency down conversion tuning.

The digital module 48 may further include a host central processing unit (CPU—not shown in FIG. 5) controlling the OCT system 20 and/or the different circuit(s), module(s) and/or component(s) included in the OCT system 20.

In the illustrated embodiment of FIG. 5, the digital module 48 includes a first and a second ADC 50, 58 and a DAC 52.

The digital module 48 may act, for example, as an acquisition and control card for controlling the OCT system 20 or the different circuits and/or components of the system 20. Without being limitative, the digital module 48 could control the optical circuit 24, the detector 38 and/or the frequency down converter described below.

Frequency Down Converter

Broadly described, the frequency down converter is configured to down convert a first signal to a second signal, the second signal having a lower frequency than the first signal. Depending on the configuration and the design of the digitization circuit 40, the frequency down converter can either be configured to down convert an analog OCT signal into a lower analog frequency signal (which will be referred in the following as the "analog implementation") or to down convert a digital OCT signal into a digitized down converted signal (which will be referred in the following as the "digital implementation"), as it will be described below.

Analog Implementation

In the analog implementation, the frequency down converter 41 is configured to down convert the analog OCT signal to a lower analog frequency signal.

The analog-to-digital converter 50 (the "ADC 50") is operatively connected to the frequency down converter 41. The ADC 50 is located downstream of the analog frequency down converter 41 and is configured to digitize the lower analog frequency signal, thereby obtaining the digitized down converted signal.

In some embodiments, the digitization circuit 40 includes a local signal generator 42 and at least one mixer 44 (referred to as the mixer(s) 44).

The local signal generator 44 is configured to generate a local oscillator signal centered around a local frequency.

The mixer(s) 44 each have a range of operation. The mixer(s) 44 is operatively connected to the local signal generator 42 and is configured to receive the analog OCT signal. The mixer(s) 44 then mixes the analog OCT signal with the local oscillator signal to obtain the down converted signal.

Figure 9:
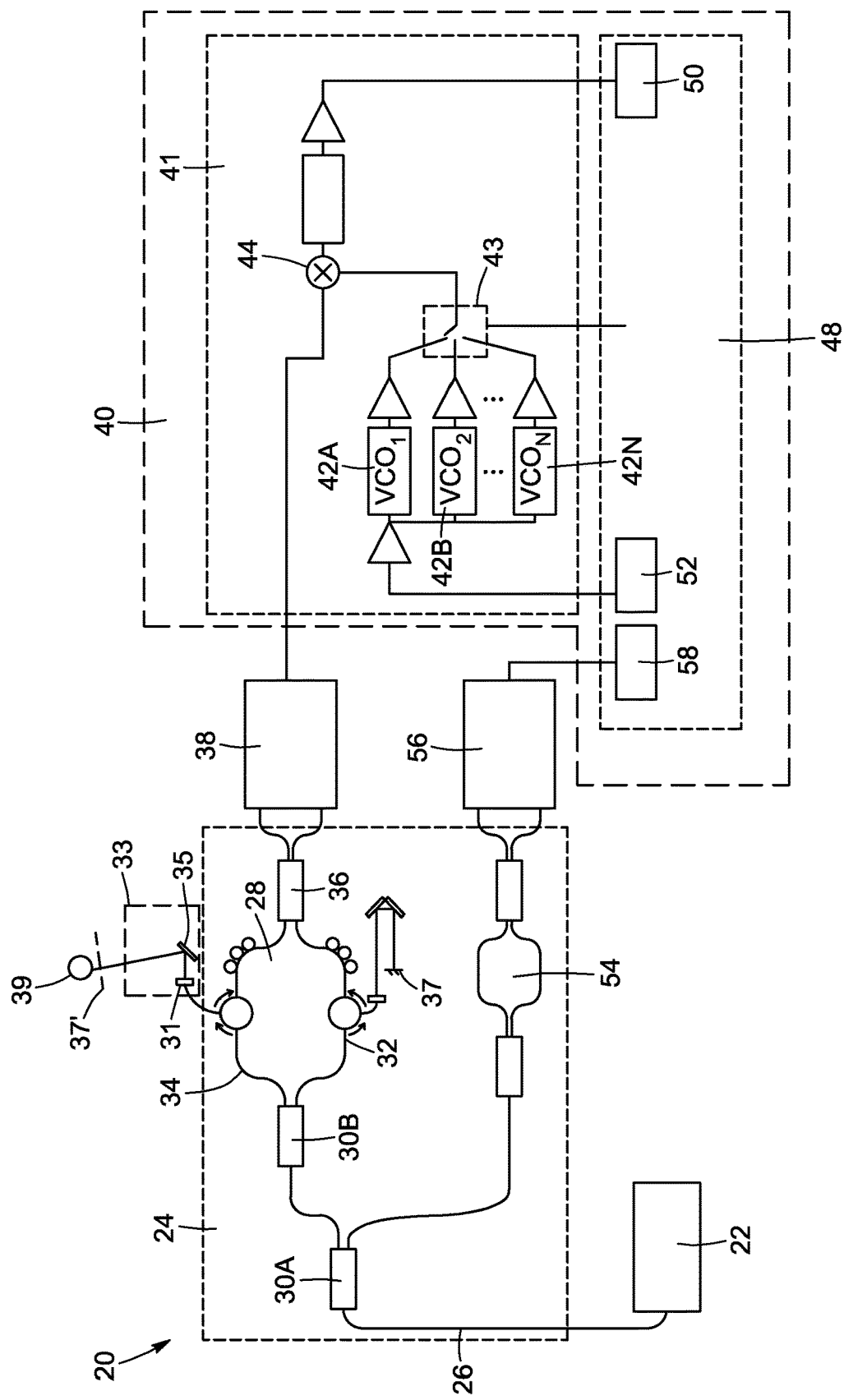
FIG. 9 illustrates a frequency down converting OCT system including a plurality of VCOs for extended bandwidth applications, in accordance with one embodiment.

In some embodiments, such as the one illustrated in FIG. 9, the local signal generator 42 comprises a plurality of voltage-controlled oscillators, each having a different bandwidth covering a corresponding portion of the range of operation of the mixer(s) 44. The digitization circuit 40 further comprises a switch to operatively connect at least one of the plurality of the voltage-controlled oscillators to the mixer(s) 44.

Figure 12:
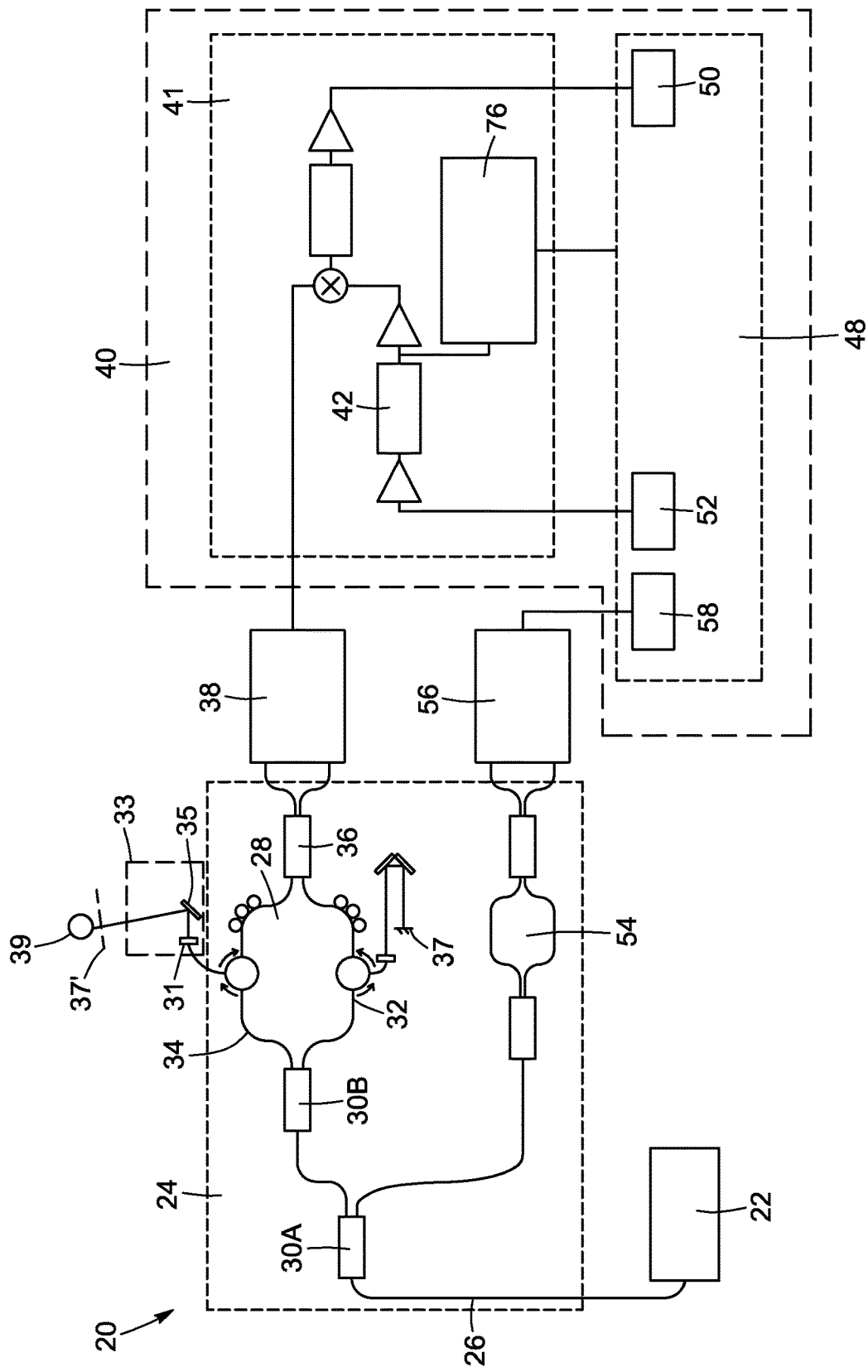
FIG. 12 illustrates a frequency down converting OCT system including a frequency counter for high accuracy ranging and profiling applications, in accordance with one embodiment.

In some embodiments, such as the one depicted in FIG. 12, the digitization circuit 40 comprises a high frequency counter 76 operatively connected to the local signal generator.

In some embodiments, the digitization circuit 40 is designed to be compatible with quadrature modulation techniques.

Figure 14:
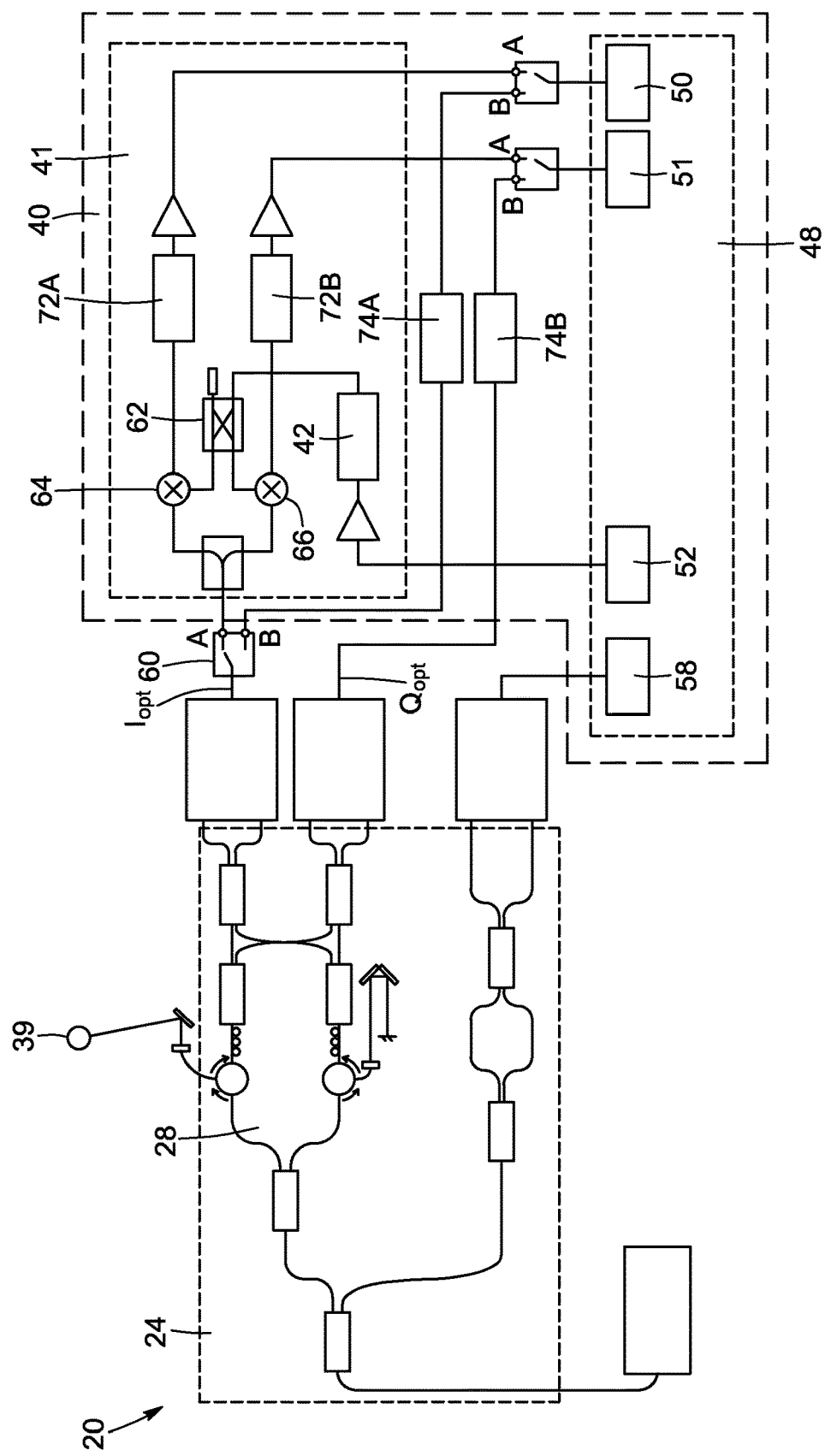
FIG. 14 is an illustration of a frequency down converting OCT system for full frequency range applications, in accordance with one embodiment.

In some embodiments, such as the one depicted in FIG. 14, the mixer(s) 44 is a pair of mixers and the OCT system 20 includes a coupler 62. As it will be presented in one of the following sections, the coupler 62 can be operatively connected to the pair of mixers 44. The coupler 62 is this embodiment configured to generate an in-phase version and an in-quadrature version of the local oscillator signal. The pair of mixers 44 is then configured to generate an in-phase down converted signal and an in-quadrature down converted signal.

In some embodiments, the analog OCT signal has a frequency in the RF domain.

In the context of the analog implementation, the digitization circuit 40 is first required to digitize this signal to obtain a sampled copy suitable for digital analysis. In some cases, this can be a limiting factor of the imaging range of traditional SS-OCT systems. As explained above, the greater the distance x between a scatterer and the image of the reference mirror, the higher the frequency of the contribution of this scatterer to the analog OCT signal. Available ADC have a maximum sampling frequency at which they are capable of faithfully reproducing an electrical signal in digital format. ADCs operating up to 500 MHz are routinely available, but the cost and complexity associated with ADCs rapidly increase above 1 GHz. Such constraints may hence limit the available imaging range which can be achieved by a SS-OCT.

For a conventional SS-OCT system, if the sample shows surface variations that are larger than that imaging range, either the entire system, the scanning head or the reference mirror has to be displaced to maintain the sample surface within the imaging range. Advantageously, in embodiments described herein the frequency down converter converts the analog OCT signal to a lower analog frequency signal, hence allowing maintaining it within the digitization capabilities of the system (i.e., the ADC 50). The imaging range may then be "displaced in space" without any moving parts.

Turning back to FIG. 5, the system 20 therefore includes the frequency down converter 41. The illustrated frequency down converter 41 shown in FIG. 5 is a simplified embodiment, and it will be readily understood by one skilled in the art that the illustrated configuration is shown by way of example only.

The frequency down converter 41 is operatively connected to the detector 38, and so is configured to receive the analog OCT signal.

As shown in FIG. 5, the frequency down converter 41 includes a local signal generator 42 generating a local oscillator signal. The local oscillator signal is centered around a local frequency. The local signal generator 42 may be a variable frequency signal generator, such as a voltage-controlled oscillator (VCO) to produce the local oscillator signal. VCOs are well known in the art as devices whose oscillation frequency may be controlled by a voltage input.

The frequency down converter 41 also includes at least one mixer 44 operatively connected to the detector 38 and to the local signal generator 42. The mixer 44 is configured to mix the analog OCT signal and the local oscillator signal, and to produce the down converted signal centered around the lower center frequency. The down converted signal is sometimes referred to as the "intermediate frequency" in the RF domain.

The down converted signal has a spectral profile comparable (i.e., substantially similar) to the spectral profile of the analog OCT signal prior to its down conversion. The lower center frequency is however generally smaller than the high center frequency of the analog OCT signal. Additional electronics components 46, such as amplifiers and filters, are generally part of the frequency down converter 41 for adapting the local oscillator signal amplitude, but also for ensuring a proper functioning and performance of the mixer 44. Such additional electronics components 46 may be also useful to reject unwanted spurious signals.

In the scenario in which the optical circuit 24 generates more than one optical interferometric beam (and so more than one corresponding analog OCT signal to be digitized), the frequency down converter 41 is adapted to have multiple channels.

In the illustrated variant of FIG. 5, the first ADC 50 receives and digitizes the lower analog frequency signal and the DAC 52 is operatively connected to the local signal generator 42. The local frequency of the local oscillator signal may be controlled by the CPU through a voltage controller and/or other means.

In operation, the analog OCT signal passes through point (a) of the system 20 and subsequently through the frequency down converter 41, before being sent to the digital module 48 (i.e., after passing through point (b) of the system 20). Passage of the analog OCT signal through the frequency down converter 41 allows down converting the frequency of the analog OCT signal from the high to the lower center frequency.

Still referring to FIG. 5, the system 20 may also include a Mach-Zehnder interferometer to generate a k-clock signal. As the optical frequency of the light source 22 is tuned during a sweep, the intensity profile at the output of the Mach-Zehnder interferometer varies from a destructive to a constructive interference pattern, hence producing an intensity modulated optical signal that is used to monitor the linearity of the optical frequency sweep. This configuration of the Mach-Zehnder interferometer is known in the art as a k-clock generator, and will be herein referred to as the "k-clock generator 54". While the k-clock is herein described in the context of analog implementations, it is to be noted that the k-clock is also compatible with digital implementations.

In the illustrated variant, the k-clock generator 54 is part of the optical circuit 24 and is operatively coupled with the light source 22 through the beam splitter 30A. As previously mentioned, the laser beam is separated into the measurement beam and the clocking beam after its passage through the first beam splitter 30A. The clocking beam enters the k-clock generator 54. The optical signal coming out of the k-clock generator 54 is converted into a k-clock electrical signal with a second detector 56. The k-clock electrical signal can then be used to trigger the ADC 50. In that case, the k-clock electrical signal will generally have to be conditioned into a signal compatible to the ADC 50. Such signal conditioning generally takes the form of amplification, AC coupling and zero-crossing detection. Alternatively, the k-clock signal can also be digitized as well with an ADC 58 to monitor the sweep departure from perfect linearity. Phase extraction and unwrapping techniques known in the art can then be applied to recover the precise optical frequency sweep profile. This profile can then be taken into account in the Fourier analysis of the down converted and digitized analog OCT signal to obtain a corrected A-scan.

The k-clock generator 54 may directly or indirectly clock the ADC 50. For example, in some embodiments, the clock 54 is operatively connected with a second detector 56 (similar to the first detector 38). The second detector 56 is operatively connected to the second ADC 58 provided in the digital module 48. In such configuration, the clock 54 is said to indirectly clock the ADC 50, through the intermediate of the second detector 56 and the digital module 48, via the ADC 58.

In some embodiments, the k-clock generator is integrated with the swept source laser 22. In other embodiments, a k-clock is generated by an electronic circuit without the need of an optical interferometer.

The optical circuit 24 and the clock 54 may be integrated into a single device or system, so as to be optically, electrically and/or mechanically connected through appropriate means and/or components.

It will be understood that the frequency down converter 41 may be configured to be compatible with the IQ technique in the electrical domain thus allowing the tuning of the local oscillator within the spectral profile of the analog OCT signal. For example, a 90° hybrid RF coupler could be used to send an in-phase and in-quadrature version of the local signal to a pair of mixers to generate the I and the Q down converted signal for digitization. This configuration hence requires two ADCs: one for digitizing the I signal, and the other for digitizing the Q signal. However, this configuration is less demanding on the required digitization bandwidth of the ADCs. For example, two ADCs having a bandwidth of 500 MHz could be used (when the frequency down converter 41 is configured to be compatible with the IQ technique), instead of only one ADC having a bandwidth of 1 GHz (when the frequency down converter 41 is not configured to be compatible with the IQ technique).

In some embodiments, the OCT system 20 includes a servo-loop. The servo-loop is configured to maintain the local frequency close to a frequency of the analog OCT signal. As it is already known in the art, the servo-loop typically includes a system to control, a measurement of a parameter to be controlled, a controller for calculating a command based on the measurement of the parameter and an actuator acting on the system. As illustrated in FIG. 5, the servo-loop includes a controller 78 and a frequency estimator unit 79. The frequency estimator unit 79 is configured to analyze the signal of the ADC 50. The controller 78 is configured to analyze the frequency estimation outputted from the frequency estimator unit 79 and to calculate the command to be sent to the DAC 52. More particularly, the frequency estimator unit 79 analyzes the signal outputted at the point b and estimates the frequency of the peak intensity signal using different methods, such as filtering, fast Fourier transform analysis, wavelet, or any other methods already known in the art. The controller 78 is then used to maintain the frequency at the point b within a predetermined frequency window (e.g., Nyqvist limit). Upon the determination of the frequency at which the local signal generator 42 is to be operated, the controller 78 sends an appropriate command towards the local signal generator 42, through the DAC 52, which in turn allows a predetermined frequency to be reached at the mixer 44. As such, the DAC 52 and the local signal generator 42 form an "actuator" performing an actuation step, based on the output of the frequency estimator unit 79.

Digital Implementation

In some variants, the OCT system that is compatible with the digital implementation is similar to the OCT system compatible with the analog implementation (as described above), except for the configuration of the digitization unit 40, as it will be explained below.

Because ADC can have an analog input bandwidth that is higher than their digitization frequency, ADC can therefore be used for digitizing bandwidth limited signals with central frequencies as high as their analog input bandwidth, provided that the signal bandwidth is smaller than half their digitization frequency. In this context, frequency down conversion OCT can be implemented using digital down conversion (DDC), as described below.

Figure 15:
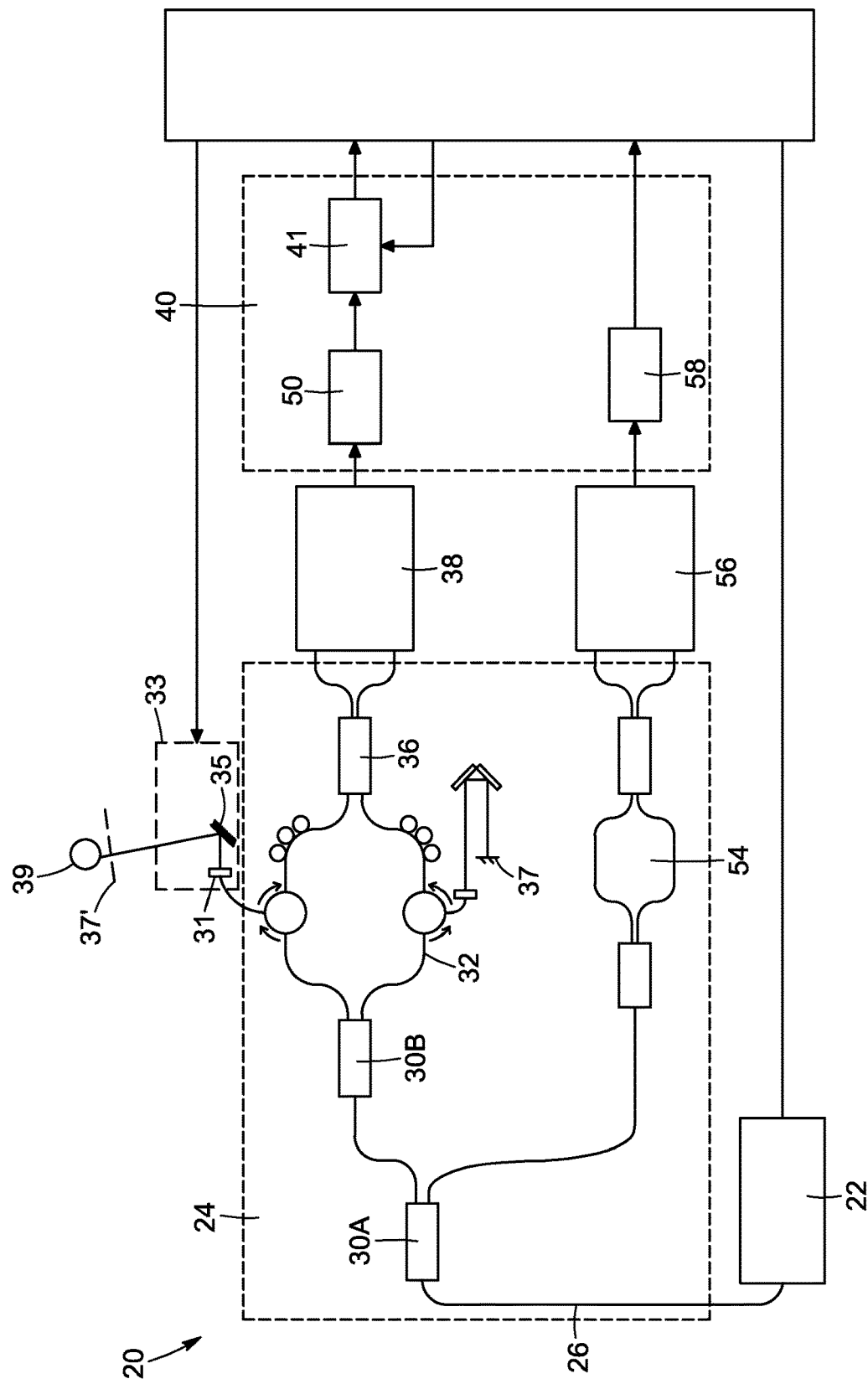
FIG. 15 is a schematized representation of a frequency down converting OCT system for imaging a sample according to one embodiment.
Figure 16:
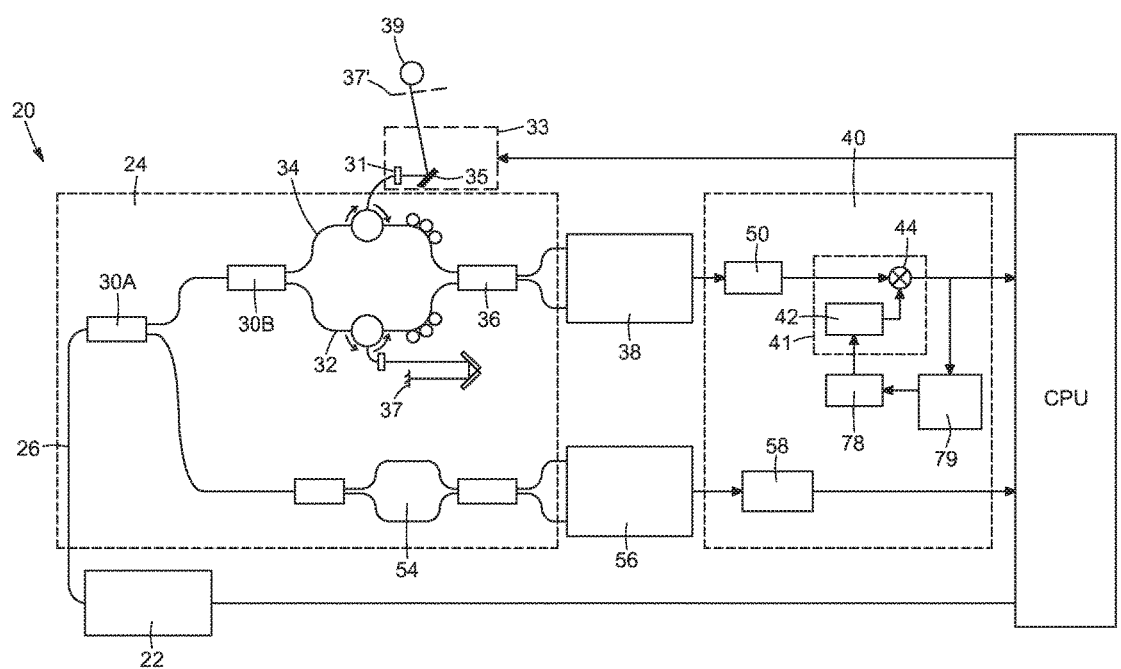
FIG. 16 is a schematized representation of a frequency down converting OCT system for imaging a sample according to one embodiment.

Now turning to FIGS. 15 and 16, the OCT system 20 according to the digital implementation also includes an ADC 50 and a frequency down converter 41. However, the ADC 50 is configured to first digitize the analog OCT signal, thereby obtaining a digital OCT signal, prior to its down conversion.

The frequency down converter 41 is operatively connected to the ADC 50 and is located downstream of the ADC 50. The frequency down converter 41 is then configured to down convert the digital OCT signal into the digitized down converted signal.

In some embodiments, the digitization circuit 40 includes a digital local signal generator 42 and a digital mixer 44.

The digital local signal generator 42 is configured to generate a digital local oscillator signal centered around a local frequency. In some embodiments, the digital local signal generator 42 is a numerically-controlled oscillator.

The digital mixer 44 is operatively connected to the digital local signal generator 42 and is configured to receive the digital OCT signal. The digital mixer 44 then mixes the digital OCT signal with the digital local oscillator signal to obtain the down converted signal.

In some embodiments, the down converted signal can be decimated by carrying out methods for reducing the data rate. It is to be noted that such methods are known in the art.

In some embodiments, the OCT system 20 includes a servo-loop similar to the one which has been described in the analog implementations. However, in the digital implementation, the actuation step is carried through writing in the register of an NCO of the digital mixer 44 (rather than using a local signal generator, as it is the case in the analog implementations).

Now that the OCT system has been described and various embodiments and implementations presented, examples of applications using the OCT system will now be presented.

Examples of Applications

Some of the applications described herein below are compatible with the analog implementation of the OCT system only, while other the examples are compatible with both the analog and digital implementations of the OCT system.

It is to be noted that the following examples are for illustrative purpose only and should therefore not be considered as being limitative.

Extended Bandwidth Variant

The extended bandwidth variant is compatible with the analog implementation of the OCT system.

As previously mentioned, the local signal generator 42 may be a VCO. While the VCOs typically have a limited bandwidth, the mixer 44 may have a range of operation extending over a larger bandwidth. It may then be necessary to use a plurality of VCOs having different bandwidth to cover the range of operation of the mixer 44, and accordingly extend the working distance range of the system 20.

Figure 8:
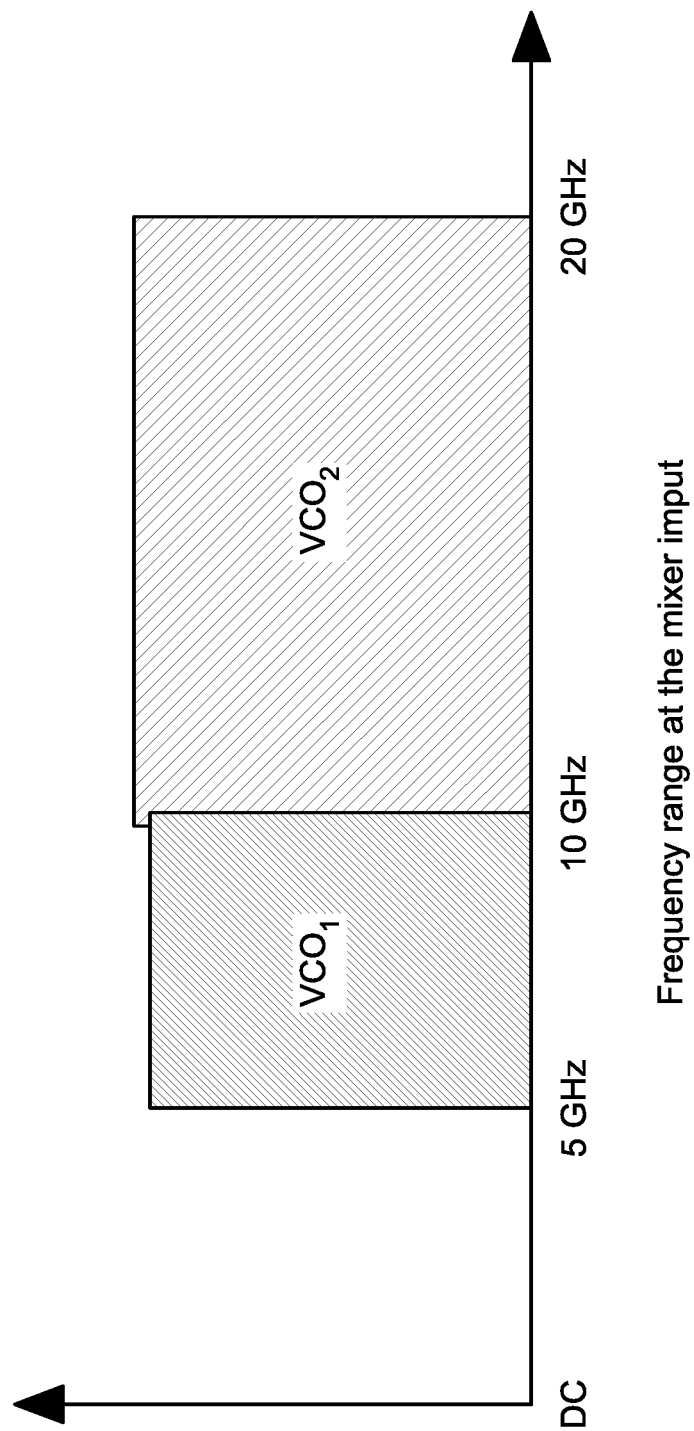
FIG. 8 illustrates a range of operation of a mixer (at the input), in accordance with one embodiment.

With reference to FIG. 8, the range of operation of the mixer 44 may extend, for example and without being limitative, from 0 to 20 GHz. In the depicted scenario, serving the purpose of an example only, two VCOs are used: a first VCO (noted by "VCO1") and a second VCO (noted by "VCO2"), each having a different bandwidth, hence each covering a portion of the range of operation of the mixer 44. In the illustrated variant, the first VCO has a bandwidth extending from 5 to 10 GHz, while the second VCO has a bandwidth extending from 10 to 20 GHz. As such, the first and second VCOs cover 75% of the frequency range of operation of the mixer (i.e., from 5 to 20 GHz). At least a portion of the remaining 25% of the frequency range of operation at the mixer 44 input (extending from 0 to 5 GHz) could be partially covered by at least one other VCO, provided that the lowest operation frequency of any VCO does not overlap with the digitization bandwidth of the ADC 50. More particularly, the lowest operation frequency of the VCO used to cover the remaining portion of the frequency range of operation of the mixer may be selected so as to not affect the precision of the digitization of the down converted signal.

Now referring to FIG. 9, an OCT system 20 including a frequency down converter 41 having a plurality of VCOs is shown. In the illustrated variant, the frequency down converter 41 includes a plurality of VCOs (each individual VCO being numbered 42A, 42B, . . . , 42N, wherein «N» is an integer representative of the number of VCOs used). Each VCOs may have a corresponding and complementary bandwidth, so as to cover a portion or the entirety of the range of operation of the mixer 44, when used in combination. The VCOs 42A, 42B, . . . , 42N are operatively connected to each other. For example, the VCOs 42A, 42B, . . . , 42N may be connected in parallel and further connected to a switch 43. The switch 43 may be configured to operatively connect at least one of the plurality of VCOs with the mixer 44, and so may be used to selectively operate at least one of the plurality of VCOs. It will be readily understood that the configuration of the VCOs 42A, 42B, . . . , 42N may be adapted and/or adjusted, for example by providing them with appropriate electronics components and devices already known by one skilled in the art.

Figure 10:
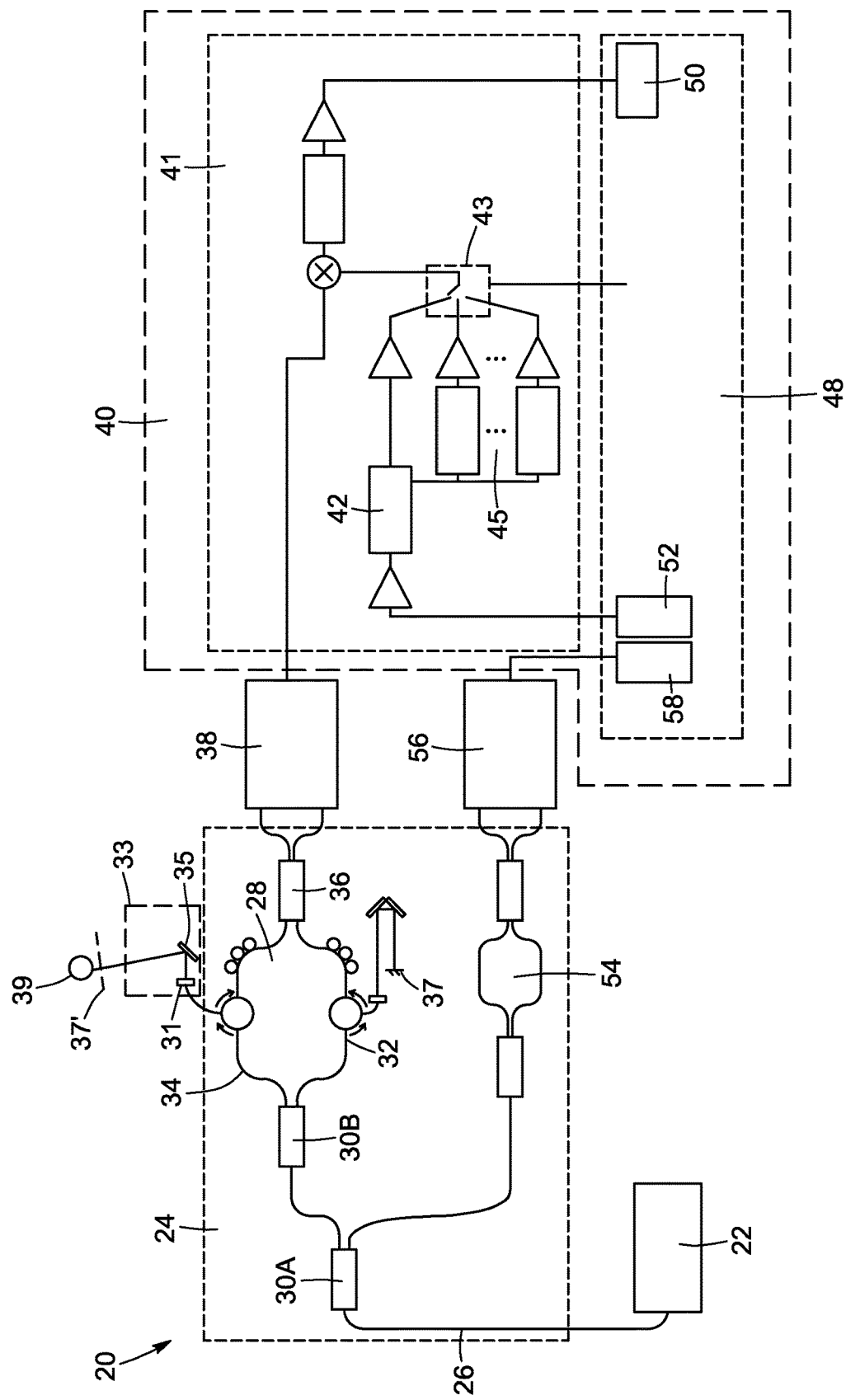
FIG. 10 illustrates a frequency down converting OCT system including an altering circuit for extended bandwidth applications, in accordance with one embodiment.

Another configuration of the system 20 may be used in the context of extended bandwidth applications. Indeed, results similar to the ones obtained with the plurality of VCOs may be achieved by using a single VCO 42 in combination with an appropriate altering circuit 45, as shown in FIG. 10. The altering circuit 45 may include, for example, one or several frequency multiplier(s) and/or divider(s), as well as appropriate electronics components to ensure an appropriate functioning of the altering circuits. Such components include, but are not limited to: resistors, switches, amplifiers, filters, and any other components already known by one skilled in the art. The combination of the local signal generator 42 and the altering circuit 45 may be useful in the context of extending the bandwidth of a single VCO. In this configuration, the switch 43 may be used to selectively operate some components of the altering circuit 45 (e.g., the frequency multiplier and/or divider).

Bandpass Sampling Variant

The bandpass sampling variant is compatible with the analog implementation of the OCT system.

The OCT system 20 may be adapted to operate in bandpass sampling mode. It is known that frequency mixer (such as the mixer 44) diverges from their ideal behavior and tends to produce unwanted replica of the signals it produces (e.g., at a different frequency than the frequency of the down converted signal, i.e. $\omega_{beat} = \omega_{OCT} - \omega_{LO}$).

The most problematic frequency is the $2\omega_{OCT} - 2\omega_{LO}$ combination, because it can limit the spur free down converted signal bandwidth. One solution to mitigate the impact of the first spur may be to use what is known in the art as "bandpass sampling" or "undersampling". In bandpass sampling, a band-limited signal is sampled at a rate lower than twice its maximum frequency.

FIG. 11A illustrates an example of a "standard sampling case" (by opposition to the "bandpass sampling case") achievable with the system presented herein. For example, the imaging range of the OCT system 20 may correspond to a 1 GHz double-sided band bandwidth. To get a spur free signal, one would have to set the local oscillator signal detuning to 1 GHz. The highest frequency is then 1.5 GHz. Respecting the Nyquist criteria would hence entails limiting the sampling frequency at 3 GHz.

For the "bandpass sampling case", illustrated in FIG. 11B, the local oscillator signal is detuned by 1.5 GHz, centering the down converted signal at 1.5 GHz, which "pushes" the first spur away, hence leaving some inter-band space to filter out the spur. It can be shown that the down converted signal can be reconstructed free of aliasing by digitizing it at twice its bandwidth, which would be in the case of the present example 2 GHz. This complementary technique (the bandpass sampling) may be used with the system 20 described herein to increase the separation between the down converted signal and the first spur, while reducing the requirements on the digitizing frequency of the first ADC 58. Of course, the numerical values presented in this example are solely illustrative and should not be interpreted as being limitative.

Accurate Sample Surface Ranging Variant

The accurate sample surface ranging variant is compatible with the analog implementation of the OCT system.

In some applications, it is important to measure the absolute distance from a reference plane to the surface of the sample. The reference plane is defined by the reference mirror image 37' (such as depicted, for example, in FIG. 5). If the local oscillator frequency is known with a very high relative accuracy, then the imaging range position with respect to the reference plane is known to that same relative accuracy. The characteristics of the local signal generator 42, for instance the local frequency of the VCOs, may be affected by temperature, supply voltage and/or other factors, and so may dynamically vary in a way that reduces the accuracy of the voltage to frequency look-up table stored in the digital module. A solution to that problem is to use a local oscillator that is itself locked to an accurate reference oscillator through what is known as a "frequency locking mechanism". This frequency locking mechanism may be, for example, embodied by a phase locked loop (PLL). In that situation, the relative accuracy of the position of the imaging range with respect to the reference plane is the same as the relative accuracy of the PLL frequency.

The response time (the time required to go from an accurately known frequency to another accurately known frequency) of the PLL circuit is generally slower than the response time of the VCO alone. This reduced response time may be limiting in situations where a fast B-scan rate is desired over a sample with abrupt change in the surface distance (i.e., when the VCO frequency may quickly vary during a short amount of time). In those applications, one solution to maintain a more precise knowledge of the local oscillator frequency for each A-scan is to monitor it with an independent frequency monitoring system.

Another variant of the system 20 is shown in FIG. 12. This variant may be useful to monitor at all time the local frequency. In order to do so, the frequency down converter 41 may include a high frequency counter 76 operatively coupled with the local signal generator 42 (e.g. the VCO). With a more accurate measurement of the local frequency for each A-scan, the imaging range may be more accurately recorded with respect to the reference plane, therefore allowing the determination of the sample surface with respect to the reference plane 37' with the same relative accuracy as the local oscillator measurement made by high frequency counter 76.

Full Frequency Imaging Range Variants

The full frequency variant is compatible with the analog implementation of the OCT system.

In conventional SS-OCT system, the OCT signal coming from a positive optical path difference (i.e., in the scenario in which the sample is placed further than the reference plane) is centered around the same frequency as the one from an equal but negative optical path difference (i.e., the scenario in which the sample is closer than the reference plane). This degeneracy limits the useful imaging range of the conventional SS-OCT system to only one of the positive or negative frequencies.

One strategy known in the art to regain the full frequency imaging range (i.e., distinguishing between the frequency associated with the positive optical path difference from the frequency associated with the negative optical path difference) is to add a detector to the OCT system 20 and to measure both the in-phase (I) and in-quadrature (Q) optical interferometric signal coming from the interferometer.

In the case of the system 20 presented in the current description, the situation may be somewhat different. Indeed, because the analog OCT signal has a relatively narrow band, the only situation where an indetermination (i.e. the degeneracy between the frequency associated with the positive optical path difference and the one associated with the negative optical path difference) occurs is in the neighboring of the zero-frequency region. In this region, the analog OCT signal is in the lower frequency band and could be digitized directly without the need for frequency down conversion.

The system 20 described with reference to FIGS. 13 and 14 may be used for applications where the full frequency imaging range is required.

FIG. 14 shows an embodiment of the system 20. Such an embodiment of the system 20 switches from a "frequency down conversion mode" to a "standard digitization mode" using signal routing switches 60, 68 and 70 to cover the full frequency imaging range supported by the bandwidth of the system 20 (i.e. the bandwidth of the detector 38).

In such an embodiment, the frequency down conversion mode is used when the analog OCT signal is of high frequency (as illustrated in FIG. 13C). In this mode, the signal routing switch 60, 68 and 70 are in position A. The analog OCT signal is transmitted towards the frequency down converter 41 before being sent toward the first ADC 50 of the digital module 48. In the other embodiments described in previous sections, the local oscillator was shown tuned close but at a lower frequency, just outside of the analog OCT signal spectrum. For this specific full frequency image range variant, the local oscillator may be tuned, for example, at the center of the analog OCT signal spectrum. This operation mode generates a degeneracy between positive and negative frequencies. One may hence need to use the IQ technique (in the electrical domain) to recover the dual-sided baseband signal. For example, a 90° hybrid RF coupler 62 (illustrated in FIG. 14) could be used to send an in-phase and in-quadrature version of the local signal to a pair of mixers 64,66 to generate the I and the Q down converted signal for digitization (as represented in FIG. 14). This IQ detection in the electrical domain is not mandatory to extending the working distance range across the full positive and negative frequencies.

The standard digitization mode is used in a low frequency range (as illustrated in FIG. 13A). In this mode, the signal routing switches 60, 68 and 70 are set to position B. The first ADC 50 and a third ADC 51 may be used to digitize the analog OCT signals (the IOPT and QOPT signals). If one only wants to extend the imaging range towards zero but not on the negative frequency side, only the IOPT signal may be recorded. However, if one wants a continuous coverage on both sides of the reference plane, then the IOPT and QOPT signals must be digitized and processed according to techniques known in the art to recover the two-sided spectrum.

The limit case of operation of this embodiment, i.e., when the system may have to switch from the frequency down conversion mode to the direct digitization mode, is shown in FIG. 13B. This case occurs when the analog OCT signal starts to overlap with its down converted version. This condition occurs at a different frequency, depending on the frequency detuning of the local oscillator with respect to the analog OCT signal spectrum. The limit case illustrated in FIG. 13B is for the situation where the local oscillator is tuned at the center of the analog OCT signal spectrum. This limit case illustrates that different low pass filters may be required for frequency down conversion operation (i.e., when switches 60, 68 and 70 are in position A) and direct digitization operation (i.e., when switches 60, 68 and 70 are in position B). For example, in the illustrated variant of FIG. 14, the frequency down converter 41 comprises a pair of low pass filters 72A, 72B for filtering the analog OCT signal after the down conversion step. The frequency down converter 41 may also include a pair of low pass filters 74A, 74B for filtering the analog OCT signal when it is centered around a relatively low frequency (i.e. when the analog OCT signal is not down converted, e.g. in the "standard digitization mode"). In the frequency down conversion mode, the pair of filters 72A, 72B may be adjusted to a specific imaging bandwidth. In the standard digitization mode, the bandwidth of the pair of filters 74A, 74B has to be large enough to cover the limit case described with reference to FIG. 13B.

Fast B-Scan Variant

The fast B-scan variant is compatible with both the analog and digital implementations of the OCT system.

Analog Implementations

In FIGS. 6A-D, it is illustrated how the system 20 may be useful in the context of a fast B-scan (in analog implementations). A fast B-scan rate may be desirable in many applications, such as the inspection of sample 39 having a curved or uneven surface (i.e., in situation in which the distance x between the reference plane 37' and the sample 39 may substantially vary along the optical axis). In a typical B-scan, the scan mirror 35 is scanned in angle to cover a line on the sample, following a procedure which has been previously mentioned. By way of example, in some embodiments, the system 20 may have a 100 kHz A-scan rate and may scan a 2048 points line. In such circumstances, the B-scan takes approximately 20 ms. It would be readily understood that the values of the A-scan rate, as well as the number of points in the line may be selected or predetermined by one skilled in the art, in accordance with the targeted applications.

One would recognize that mechanically moving some components of the system 20 (e.g., the reference mirror 37 or the scanning head 33) or the system 20 by a relevant amount over 20 ms may be very challenging, in part due the mass of the components to be moved involved. Advantageously, the down conversion SS-OCT system described herein provides a mean to vary the working distance without the need to displace such components.

FIG. 6A shows a sample's uneven surface (represented by the full line), and more particularly illustrates the variation in the distance between the reference plane 37' and the surface of the sample 39. This variation in distance is taken along the B-scan direction and is compared to the imaging range supported by "standard digitization" of conventional SS-OCT system, (illustrated by a horizontal narrow band centered around relatively high frequency, with respect with the width of the narrow band). In this example, the surface topography variations are greater than the imaging range supported by standard digitization. As such, appropriate imaging of the sample 39 cannot be successfully achieved without mechanically moving parts of the system.

Digital Implementations

In FIGS. 6E-H, it is illustrated how the system 20 may be useful in the context of a fast B-scan for the digital implementations.

While the general working principle is substantially the same, a few differences distinguish the digital implementations from the analog implementations in the context of a fast B-scan. Indeed, the main difference comes mainly from the fact that to use the digital implementations of the fast B-scan, undersampling techniques are typically used, which can result in aliasing of the signal around the sampling frequency.

A conventional SS-OCT system, such as the one is currently known in the art, may be configured with a very high digitization frequency and thus have a substantially large imaging range. As a result, such conventional SS-OCT system may be capable of imaging samples with uneven surface. However, in a vast majority of applications, OCT techniques can only see through a few millimeters within a sample as light attenuation and scattering within the sample is the predominant limiting factor on the penetrating depth of the sample beam. This implies that even though an OCT system may be conceived to have a large imaging range capable of imaging samples with highly uneven surface, the actual signal is only coming from a limited range of a few millimeters within that larger range.

FIG. 6B shows an example of the analog OCT signal. While the analog OCT signal is illustrated as being in the RF domain, it is to be noted that the analog OCT signal could be different (e.g., the signal could be a digital OCT signal, or could be a signal that is not in the RF domain), inasmuch as the analog OCT signal (or the digital OCT signal) is representative of the sample along the B-scan direction. The analog OCT signal (or the digital OCT signal) is centered around a high frequency and is characterized by a substantially narrow spectral band.

For the analog implementation of the system, the OCT system 20 may control the local signal generator 42 (e.g. a VCO, as presented in FIG. 5) to generate the local oscillator signal centered around the local frequency. The local frequency is tuned to a value relatively close to the frequency domain of the analog OCT signal for that given position on the B-Scan, as illustrated in FIG. 6C. On this aspect, the local oscillator signal is similar to the analog OCT signal, because it "follows" the general shape of the analog OCT signal.

For the digital implementation of the system, the OCT system 20 may control the local signal generator (e.g. an NCO, as presented in FIGS. 15 and 16) to generate the local oscillator signal centered around the local frequency. The local frequency is tuned to a value relatively close to the frequency domain of the digital OCT signal for that given position on the B-Scan. On this aspect, the local oscillator signal is similar to the digital OCT signal, because it "follows" the general shape of the digital OCT signal.

In order to appropriately tune the local frequency of the local signal generator, one may previously have a priori knowledge of the approximate distance between the reference plane 37' and the surface of the sample 39. More specifically, the general shape of the sample 39 (or alternatively, the surface variations) may be known before its inspection by the system 20. In the case of automated industrial inspection (e.g., paint inspection), the general shape of the sample 39 under investigation (and therefore its surface) may be known, and one may be only concerned with the depth measurements provided. The system 20, as described, hence allows such inspection.

FIG. 6D shows the down converted signal (i.e. either the analog or the digital OCT signal, once down converted) at the output of the mixer (not illustrated in FIG. 6D). As shown, the down converted signal is centered around the lower center frequency and is still characterized by its substantially narrow band.

In the analog implementation, such down converted signal is easier to digitize with respect to the original analog OCT signal (i.e. before its down conversion). Indeed, and now referring back to FIG. 5, the lower center frequency is less demanding for the sampling frequency of the digital module 48 and more particularly for the first ADC 50 digitizing the down converted signal, instead of the analog OCT signal directly outputted by the detector 38 placed at the output of the optical circuit 24.

In the digital implementations, the down converted signal can be decimated to reduce the data rate at the output of the digitization module 40. Methods for decimating a signal are already known in the art.

Adaptable Imaging Range Variant

The adaptable imaging range variant is compatible with both the analog and digital implementations of the OCT system.

Figure 7:
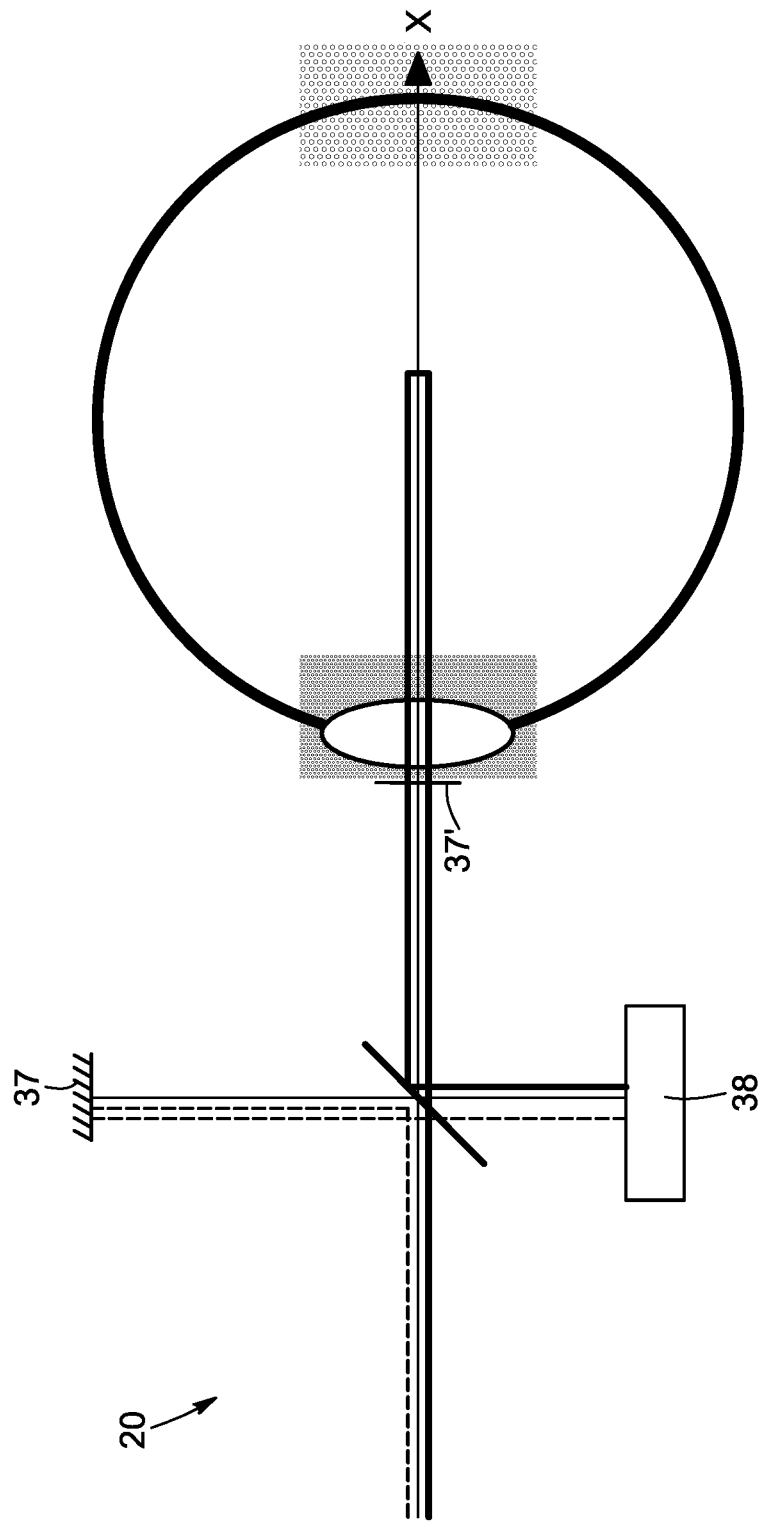
FIG. 7 is an illustration of the frequency down converting OCT system according to FIG. 2 for adaptable imaging range applications, in accordance with one embodiment.

The different configurations and operation modes of the system 20 which have been described above may be useful in another application. For example, the system 20 may have an adaptable working distance, which may be useful when it is required to quasi-simultaneously or successively provide an image representative of two points of interest of the sample. In some implementation, the two points of interest (each formed by multiple individual scatterers) may be disposed at different depths within the sample (i.e., along the optical axis or along the sample beam propagation direction). Such an example is shown in FIG. 7, wherein the working distance may be adjusted to center the imaging range either on the anterior or the posterior portions of an eye by changing the frequency of the local oscillator. The working distance may be alternated between those two positions by changing the frequency of the local oscillator. If the change in frequency is fast enough, a quasi-simultaneous image of both regions may be recorded or displayed to a user, either as a still image or a video feed.

Servo Down Conversion Tuning Variant

The servo down conversion tuning variant is compatible with both the analog and digital implementations of the OCT system.

In some scenario, the shape or the sample's surface may be unknown or poorly characterized. It may be then useful to combine the system 20 with a separate range finder or surface profiler 80 to supply the required topological information, or any other information of particular interest concerning the sample 39 (or its surface). Such range finder and surface profiler may already be known by one skilled in the art and may be adjusted in view of a specific targeted application.

Information about the sample's surface could also be extracted from the data generated by the system 20 (and digitized by the digital module 48, as illustrated in FIG. 5), and the frequency offset between the local oscillator frequency and the OCT signal frequency, for example, may be maintained through a servo-loop, such as the one which has been previously described. The servo-loop may be configured to adjust the frequency of the local oscillator signal.

In the analog implementation of the system, the ADC 50 has a digitization bandwidth and the OCT system 20 includes a servo-loop configured to maintain the down converted OCT signal within the digitization bandwidth of the ADC 50. In some embodiments, the system may track in real time for each A-scan the frequency of the down converted signal. This measurement can be done by an analysis of the digitized A-Scan data. In one variant, the system can track the frequency of the signal coming from the first surface of the sample. The signal coming from the first surface generally correspond to the highest intensity. In other variants, the system can track other statistics of the down converted analog OCT signal such as the intensity weighted average frequency or any other statistic of the signal's spectrum representative of its relative centering within the imaging range.

This down converted signal frequency measurement can then be used as the input of the controller 78 that controls the local down converter tuning frequency in an adaptive manner, so that the down converted signal is always centered within the digitization bandwidth of the digital module 48 as the B-scan progresses. In this variant, the system 20 may need to be initialized on the first A-scan, to ensure that the down converted signal is centered within the digitization bandwidth of ADC 50, so that the controller 78 can lock on the lower center frequency. In some embodiments, the initialization step could be done by sweeping the local signal generator 42 (i.e., the VCO). In other embodiments, the starting point of a preceding B-scan could be used for setting the VCO frequency for the first A-Scan of a line, assuming that the surface distance is slowly varying (or slightly varying, i.e., presenting smooth surface variations) in the C-scan direction from one B-scan to another. In this case, the local signal generator sweeping may be done only at the first A-Scan of the first B-scan, or every time the synchronization is lost, for example in the case where there is an abrupt change in the surface distance.

In the digital implementation of the system, the servo-loop is configured to maintain the local frequency close to a frequency of the digital OCT signal.

Method for Imaging a Sample

In accordance with embodiments, there is also provided a method for imaging a sample.

The method includes a step of optically probing the sample to generate an analog OCT signal representative of the sample and a step of processing the analog OCT signal to obtain a digitized down converted signal.

In some embodiments, the step of processing the analog OCT signal includes a step of digitizing the analog OCT signal to obtain a digital OCT signal, a step of down converting the digital OCT signal to obtain the digitized down converted signal, and a step of digitally filtering the digital OCT signal.

In some embodiments, the method includes a step of decimating the digitized down converted signal.

In some embodiments, the steps of digital filtering, down converting and decimating are jointly named "Digital Down Conversion" (DDC) and are the digital equivalent to analog frequency down-conversion.

In some embodiments, the step of processing the analog OCT signal includes a step of down converting the analog OCT signal to a lower analog frequency signal, a step of filtering the lower analog frequency signal in the analog domain, and a step of digitizing the lower analog frequency signal to obtain the digitized down converted signal.

In some embodiments, the method includes a step of monitoring with a high frequency counter, during an A-scan, a local frequency of a local oscillator signal generated by a local oscillator general.

It is to be noted that the method presented above (or at least one step) can be performed using the OCT system described in the previous section. It is also to be noted that the steps of the method can generally be carried out in a different order than the one which has been presented above, inasmuch as the methods allows to output a digitized down converted signal from an analog OCT signal representative of the sample.

Of course, numerous modifications could be made to the embodiments described above without departing from the scope of the current description.

The invention claimed is:

1. An optical coherence tomography (OCT) system for imaging a sample, the OCT system comprising:
   an optical circuit comprising an interferometer, the optical circuit being configured to probe the sample and generate an analog OCT signal representative of the sample;
   a digitization circuit comprising:
      a frequency down converter configured to receive the analog OCT signal from the optical circuit and down convert the analog OCT signal into a down converted signal; and
      an analog-to-digital converter having a digitization bandwidth and configured to receive the down converted signal and digitize the down converted signal to obtain a digitized down converted signal; and
   a servo-loop configured to maintain, using feedback from the digitized down converted signal, a spectrum of the down converted signal within the digitization bandwidth of the analog-to-digital converter.

2. The OCT system of claim 1, wherein the OCT system is designed as a swept source OCT system.

3. The OCT system of claim 1, further comprising a scanning head for scanning the sample, wherein the interferometer comprises a reference arm and a sample arm optically coupled to the scanning head.

4. The OCT system of claim 1, further comprising at least one optical detector coupled to the optical circuit and operatively connected to the digitization circuit.

5. The OCT system of claim 1, wherein:
   the optical circuit is configured to generate multiple analog OCT signals; and
   the digitization circuit comprises multiple channels, each channel being configured to receive one of the multiple analog OCT signals.

6. The OCT system of claim 1, further comprising a surface profiler for providing topological information about a surface of the sample.

7. The OCT system of claim 1, wherein the frequency down converter comprises:
   a local oscillator configured to generate a local oscillator signal having a spectrum centered around a local oscillator frequency; and
   at least one mixer having a range of operation, the mixer being operatively connected to the optical circuit and to the local oscillator and being configured to receive and mix together the analog OCT signal and the local oscillator signal to obtain the down converted signal.

8. The OCT system of claim 7, wherein the local oscillator is a voltage-controlled oscillator.

9. The OCT system of claim 7, wherein the local oscillator comprises a plurality of voltage-controlled oscillators, each having a different bandwidth covering a corresponding portion of the range of operation of said at least one mixer, the digitization circuit further comprising a switch to operatively connect at least one voltage-controlled oscillator of the plurality of voltage-controlled oscillators to said at least one mixer.

10. The OCT system of claim 7, wherein the digitization circuit comprises a high frequency counter operatively connected to the local oscillator.

11. The OCT system of claim 7, wherein the digitization circuit is designed to be compatible with quadrature modulation techniques.

12. The OCT system of claim 11, wherein said at least one mixer is a pair of mixers and the OCT system further comprises:
   a coupler operatively connected to the pair of mixers, the coupler being configured to generate an in-phase version and an in-quadrature version of the local oscillator signal, the pair of mixers being configured to generate an in-phase down converted signal and an in-quadrature down converted signal.

13. The OCT system of claim 1, wherein the analog OCT signal has a frequency in the RF domain.

14. An optical coherence tomography (OCT) system for imaging a sample, the OCT system comprising:
   an optical circuit comprising an interferometer, the optical circuit being configured to probe the sample and generate an analog OCT signal representative of the sample;
   a digitization circuit comprising:
      an analog-to-digital converter configured to receive the analog OCT signal from the optical circuit and digitize the analog OCT signal, thereby obtaining a digital OCT signal; and a frequency down converter located downstream of the analog-to-digital converter and configured to down convert the digital OCT signal into a digitized down converted signal, the frequency down converter comprising:
  a local oscillator configured to generate a local oscillator signal having a spectrum centered around a local oscillator frequency; and
  a mixer operatively connected to the analog-to-digital converter and to the local oscillator, the mixer being configured to receive and mix together the digital OCT signal and the local oscillator signal to obtain the digitized down converted signal; and
a servo-loop configured to maintain, using feedback from the digitized down converted signal, the local oscillator frequency to within a frequency offset from a frequency of the digital OCT signal.

15. The OCT system of claim 14, wherein the local oscillator is a numerically-controlled oscillator.

16. The OCT system of claim 14, wherein the OCT system is designed as a swept source OCT system.

17. The OCT system of claim 14, further comprising a scanning head for scanning the sample, wherein the interferometer comprises a reference arm and a sample arm optically coupled to the scanning head.

18. The OCT system of claim 14, further comprising at least one optical detector coupled to the optical circuit and operatively connected to the digitization circuit.

19. The OCT system of claim 14, wherein:
the optical circuit is configured to generate multiple analog OCT signals; and
the digitization circuit comprises multiple channels, each channel being configured to receive one of the multiple analog OCT signals.

20. The OCT system of claim 14, further comprising a surface profiler for providing topological information about a surface of the sample.

21. An optical coherence tomography (OCT) method for imaging a sample, the OCT method comprising the steps of:
  optically probing the sample to generate an analog OCT signal representative of the sample;
  processing the analog OCT signal to obtain a digitized down converted signal, said processing comprising:
    down converting the analog OCT signal to obtain a down converted signal; and
    digitizing the down converted signal with an analog-to-digital converter having a digitization bandwidth to obtain a digitized down converted signal; and
  maintaining, with a servo-loop using feedback from the digitized down converted signal, a spectrum of the down converted signal within the digitization bandwidth of the analog-to-digital converter.

22. The method of claim 21, wherein down converting the analog OCT signal to obtain the down converted signal comprises:
  generating a local oscillator signal having a spectrum centered around a local oscillator frequency; and
  receiving and mixing together the analog OCT signal and the local oscillator signal to obtain the down converted signal.

23. The method of claim 22, further comprising a step of monitoring with a high frequency counter, during an A-scan, the local oscillator frequency of the local oscillator signal generated by a local oscillator.

24. An optical coherence tomography (OCT) method for imaging a sample, the OCT method comprising the steps of:
  optically probing the sample to generate an analog OCT signal representative of the sample;
  processing the analog OCT signal to obtain a digitized down converted signal, said processing comprising:
    digitizing the analog OCT signal to obtain a digital OCT signal;
    down converting the digital OCT signal, said down converting comprising
      generating a local oscillator signal having a spectrum centered around a local oscillator frequency; and
      receiving and mixing together the digital OCT signal and the local oscillator signal to obtain the digitized down converted signal; and
  maintaining, with a servo-loop using feedback from the digitized down converted signal, the local oscillator frequency to within a frequency offset from a frequency of the digital OCT signal.

25. The method of claim 24, further comprising a step of decimating the digitized down converted signal.

* * * * *